United States Patent
Watkins et al.

(10) Patent No.: US 6,690,016 B1
(45) Date of Patent: *Feb. 10, 2004

(54) PROCESS CONTROL BY TRANSIENT THERMOGRAPHY

(75) Inventors: Michael L. Watkins, Chester, VA (US); Grier S. Fleischhauer, Midlothian, VA (US); A. Clifton Lilly, Jr., Chesterfield, VA (US)

(73) Assignee: Philip Morris Incorporated, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/600,298

(22) PCT Filed: Feb. 10, 1999

(86) PCT No.: PCT/US99/02672

§ 371 (c)(1),
(2), (4) Date: Dec. 6, 2000

(87) PCT Pub. No.: WO99/40417

PCT Pub. Date: Aug. 12, 1999

Related U.S. Application Data

(63) Continuation of application No. 09/021,224, filed on Feb. 10, 1998, now Pat. No. 6,013,915.

(51) Int. Cl.[7] .............................. G01J 5/02; G01N 25/72
(52) U.S. Cl. ............................... 250/341.7; 250/341.1; 250/341.6; 250/341.8; 250/359.1; 374/5
(58) Field of Search .................. 250/341.7, 341.1, 250/341.6, 341.8, 358.1, 359.1; 374/5, 7, 124

(56) References Cited

U.S. PATENT DOCUMENTS

| | | | | |
|---|---|---|---|---|
| 4,818,118 A | * | 4/1989 | Bantel et al. | 250/341.6 |
| 5,032,727 A | | 7/1991 | Cox, Jr. et al. | |
| 5,075,552 A | | 12/1991 | McClelland et al. | |
| 5,111,048 A | | 5/1992 | Devitt et al. | |
| 5,305,893 A | * | 4/1994 | Hereford | 198/360 |
| 5,444,241 A | | 8/1995 | Del Grande et al. | |
| 5,582,485 A | | 12/1996 | Lesniak | |
| 5,659,624 A | | 8/1997 | Fazzari et al. | |
| 5,705,821 A | | 1/1998 | Barton et al. | |
| 5,711,603 A | | 1/1998 | Ringermacher et al. | |
| 5,827,549 A | | 10/1998 | Rancich et al. | |
| 5,833,452 A | * | 11/1998 | Donelson et al. | 198/360 |
| 6,000,844 A | * | 12/1999 | Cramer et al. | 428/457 |
| 6,013,915 A | | 1/2000 | Watkins | |
| 6,346,704 B2 | * | 2/2002 | Kenway | 250/330 |

FOREIGN PATENT DOCUMENTS

| | | | | |
|---|---|---|---|---|
| EP | 89760 A2 | * | 9/1983 | G01N/25/72 |
| WO | WO 9805921 A1 | * | 2/1998 | G01B/11/06 |

* cited by examiner

*Primary Examiner*—Albert Gagliardi
(74) *Attorney, Agent, or Firm*—Burns, Doane, Swecker & Mathis, LLP

(57) ABSTRACT

A method and apparatus for detecting, locating, isolating and controlling variations in the manufacturing process by transient thermography. A heat source (200) imparts heat to a surface which is radiated in the infrared region. Infrared sensors (204, 206, 208, 210) are coupled to a processor which tracks the physical characteristics of the sample, and provides feedback to a central process controller to make adjustments to the manufacturing process. The sample can be a continuous product such as a green powder metal sheet or tobacco product.

64 Claims, 21 Drawing Sheets

PROCESS CONTROL BY TRANSIENT THERMOGRAPHY

RELATED APPLICATIONS

This application is a U.S. National Stage application of International Application No. PCT US99/02672, filed Feb. 10, 1999, and which is a continuation of application Ser. No. 09/021,224, filed on Feb. 10, 1998, now U.S. Pat. No. 6,013,915.

FIELD OF THE INVENTION

The present invention relates to an apparatus, system and method for the production of high-quality materials. More specifically, the present invention relates to the thermal inspection of materials, location and/or geometry of defects in those materials, and providing of feedback into a processing control to identify, reduce, and remove the incidences of defect production in the material.

DESCRIPTION OF THE RELATED ART

Thermography is generally known. It is used, e.g., in probing aircraft surfaces and other materials for hidden cracks and flaws.

U.S. Pat. No. 5,711,603 discloses a transient depth thermography technique for the nondestructive testing of objects. The method includes steps of heating the surface of an object, recording pixel intensity for each pixel in a heated surface, and determining pixel contrast from pixel intensity. The method monitors the pixel contrast over successive images to determine the location of a flaw within an object and the surface can be depicted on a print which correlates the flaws with their depth coded by color.

U.S. Pat. No. 5,705,821 discloses a method and apparatus for checking IC chips for defects by scanning fluorescent microthermal imaging. The method uses a scanned and focused laser beam to excite a thin fluorescent film disposed on the surface of an integrated circuit chip. Localized heating associated with IC chip defects is observed by collecting fluorescent radiation from the film and forming a thermal map.

U.S. Pat. No. 5,582,485 discloses a method of analyzing structures by time-varying thermal signals. A projector projects a moving pattern of heat onto a test object, and an infrared camera insensitive to the projected wavelength detects emitted heat from the object. Variances in the pattern are caused by heat buildup by resistance to downward and lateral flows of heat energy, and thus may detect cracks and debonding simultaneously.

U.S. Pat. No. 5,444,241 discloses a dual-band infrared imaging method. Computerized tomography images the structure using infrared radiation. A structure to be imaged is heated by at least two different wavelengths of infrared radiation, images are sequentially obtained, and the images are utilized to determine whether a flaw is present.

U.S. Pat. No. 5,032,727 discloses the detection of defects in manufactured products by thermal ratio analysis, which is said to involve the ratios of thermal data and their analysis including statistical analysis. Also disclosed is image enhancement and the rejection of known artifacts.

SUMMARY OF THE INVENTION

The present invention provides an apparatus and method for improving product quality of products produced by batch or continuous processes wherein one or more process variables are controlled as a function of at least one product characteristic monitored during manufacture thereof. Alternatively, the apparatus and method can be used to identify the location and/or geometry of flaws in material produced by a continuous or batch process.

According to one embodiment of the invention, the apparatus can include a central process controller, a thermal gradient initiator, an infrared detector and a computer. The controller can include hardware and/or software effective to control one or more process variables during manufacture of a product in a manufacturing line, the thermal gradient initiator can provide a thermal gradient within the product at a location along the manufacturing line, and the infrared detector can be positioned to receive a thermographic image of the product at or downstream of the thermal gradient initiator. The computer preferably includes hardware and/or software to communicate with the central process controller, receive and analyze the image from the infrared detector, and determine at least one physical characteristic of the product, and output data corresponding to the determined physical characteristic to the central process controller. The central process controller can also modify one or more of the process variables when the determined physical characteristic is outside a range of predetermined values for the physical characteristic.

According to another embodiment of the invention, the apparatus can be used for inspecting a sheet material produced by a production process having a process flow wherein the apparatus includes a central process controller, a source of incident radiation, a conveyor, an infrared detector, and a computer. The central process controller can be configured to control at least one aspect of the production process, the source of incident radiation can be arranged to impinge upon the sheet material, the conveyor can be arranged to move the sheet material in a single plane, and the infrared detector can be located proximate to a surface of the sheet material so as to create an image of the surface of the sheet material at or downstream of the source of incident radiation. The computer can be in communication with the central process controller and configured to receive and analyze the image from the infrared detector to determine physical characteristics of the sheet material, and transmit the determined physical characteristics to the central process controller, so that the central process controller adjusts the at least one aspect of the production process in response to the determined physical characteristic.

DETAILED DESCRIPTION OF THE PREFERRED EMBODIMENT

Figure 1:
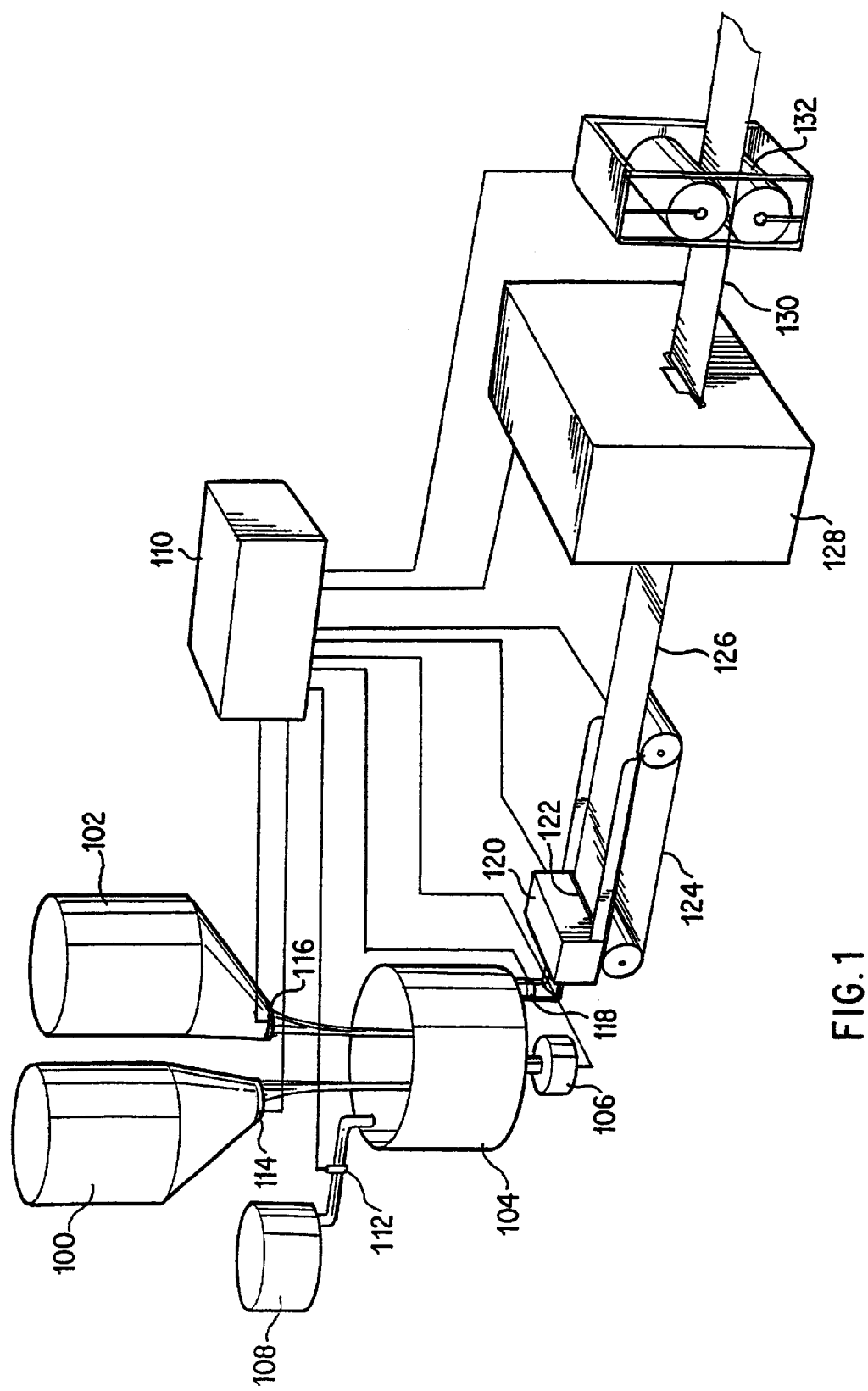
FIG. 1 is a perspective view of a production line for the manufacture of an alloy material according to the present invention.

The apparatus and method according to the invention can be used in conjunction with processing batch or continuously produced materials in particulate or solid form. According to preferred embodiments, the processed materials include continuously produced metal powder articles such as sheet material and non-metallic materials such as tobacco products. The apparatus and method can be used for real time control of process variables or for identifying locations and/or geometries of flaws in the processed material.

To ensure the quality of a processed material, the present invention contemplates utilizing the anisotropic heat flow properties of an irregular manufactured material to detect and control variations in the manufacturing process. Additionally, the present invention contemplates the supplying of additional useful processing data by decoupling certain measurements, e.g. thickness and density, to enable optimized process control. Furthermore, the invention can achieve locating and isolating the geometry of defective material in a process stream to provide a high quality output.

The present invention can provide various advantages including the production of reliably high quality materials in a manufacturing process by means of a defect detection system which will provide indication of defects in partially processed materials before their processing is complete to reduce waste. If desired, the system can include a feedback loop system for controlling a manufacturing process on-line to reduce the amount of waste material produced. For example, the system can provide on-line component control for a manufacturing process via a feedback system to allow for real time adjustment of the process. In carrying out the process, images of the material manufactured can be used to indicate the presence or absence of flaws as a quality control checkpoint. In the process it is possible to obtain individual datum on physical characteristics of a material instead of coupled data from a plurality of characteristics. In an exemplary embodiment, a material is formed into a continuous product such as a powder metallurgical green sheet or sheet of tobacco, a composite of materials such as metallic or non-metallic substances, a composite of materials such as metal, ceramic or organic substances including tobacco coated mat, etc.

The apparatus and method according to a first embodiment of the present invention may perhaps be best understood with reference to a specific end use e.g. the manufacture of alloys by various processes. The following discussion is for illustration and should not be construed as a limitation to the scope of the invention.

Alloy manufacture via powder metallurgy requires numerous specific processing steps and discrete component additions to result in an alloy having precisely calibrated properties. Even minor deviations from preselected characteristics of processing may result in flawed or unusable materials. The alloy can be characterized by uniformity, particle size, thickness, and various other parameters which will affect the final product characteristics. Of particular importance, processing of alloy materials when they are in their earliest formative steps, e.g. as a so-called "green sheet" requires a particularly noninvasive type of analysis.

For example, alloys used as electrical resistance heating elements require specific resistances to achieve a certain temperature while drawing a certain current. The alloys must also resist a tendency to creep, oxidize, or otherwise degrade over extended cycling through high temperatures. These characteristics are frequently tied to the alloy components, but it should be noted that they are also directly related to various processing steps.

It would be desirable to detect problems arising during the processing of the materials in a manufacturing process and rejection of those materials with concomitant correction of the manufacturing process to reduce waste and excess costs associated therewith. It is far cheaper to detect a flawed batch of materials than to replace a heater in, for example, a toaster, electrical smoking system, a filament in a light bulb, or the like. It is also desirable to conduct such an analysis with a noninvasive procedure, e.g. one of the present invention which causes minimal temperature changes, on the order of magnitude of 1–10 degrees, especially 2 to 5° C. However, the temperature change can be higher, such as up to 100° C., provided that the temperature change does not adversely affect the material being processed (e.g., a temperature change which would degrade the binder in the case of processing green sheet).

Turning now to FIG. 1, where is illustrated one method of manufacturing an alloy, one can see the various components of the process. Alloy raw materials, which may be in powdered form, are contained in bins 100 and 102. Any number of bins may be added as appropriate for the alloy content. Indeed, some of the bins may contain premixed powders or the like depending on the specific alloy formulation chosen for manufacture. By way of example, bin 100 can contain iron powder and bin 102 can contain aluminum powder for use in a tape casting process. Other processes of consolidating powder metallurgical products, such as coldrolling of elemental powders, may be used and chosen by one of skill in the art. For purposes of the present discussion, the process of the invention will be explained with reference to a tape casting process.

Each bin empties into mixing vessel 104 which is churned or mixed by motor 106 connected to mixing blades or other means (not shown). Bin 108 contains a binder system. Bin 108 empties into mixing vessel 104 as well. Controller 110 determines the rates of flow of the component materials, and thus the ultimate alloy composition, by sending signals to valves 112, 114, and 116 to control their rates of flow into the mixture. Such control may also be maintained by pumps, conveyors, etc.

The mixture exits mixing vessel 104 and passes through valve 118 into headbox 120. Headbox 120 has an orifice 122 proximate to a moving endless conveyor belt 124. Orifice 122 is height adjustable. The mixture emerges, e.g. by extrusion, from orifice 122 onto conveyor 124 to form a tape casting 126. The tape casting passes through a chamber 128 which can apply heat (e.g. flash drying) or vacuum for removal of binder in varying amounts.

Such drying forms a "green sheet" 130. The green sheet 130 may then be processed by rolling in a rolling mill 132. Optionally, further steps such as annealing and additional hot or cold working, e.g. extrusion, rolling, drawing, etc. may be conducted upon the green sheet.

It may be seen that careful process control is necessary throughout the above process to yield an end product with appropriate thickness, constituents, consistency, particle sizes, and the like.

The green sheet, after it has stabilized at least in part, may be inspected at various locations along the path of processing. For example, if the casting machine has a sufficiently long conveyor such that the sheet is self-supporting, an inspection station may be established prior to debindering and flash drying. An inspection station may also be established after the drying/debindering step, and after the rolling step.

Figure 2:
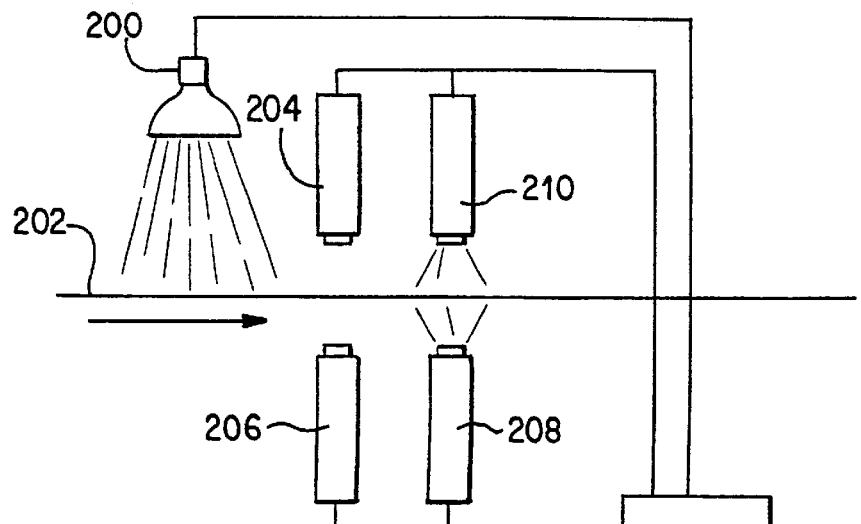
FIG. 2 is a side view of a transient thermography inspection system according to the present invention.

An exemplary generic inspection station is illustrated in FIG. 2. Heat source 200 throws radiation upon surface 202. The radiation may be visible, ultraviolet, infrared, or even magnetic induction. A particularly preferred embodiment includes monochromatic, e.g. laser, light focused in a band, to a point, or other spatial pattern. Especially preferred embodiments include temporal modulation, e.g. a pulsed source with pulses occurring in a frequency of from 1 to 500 Hz. Especially suitable for this invention is a pulse of from 50 to 150 Hz, more especially about 100 Hz.

A suitable lamp is, e.g. a Balcar 6.4 kJ xenon flash lamp with associated power supply manufactured by Balcar, Inc., France. A suitable laser is a Magnum Diode Laser (4 watts) with associated optics (line, spot, grid optic generator) manufactured by Lasiris, Inc., Quebec, Canada.

The surface is in one embodiment traveling in the direction of the arrow in FIG. 2. Such a process would be a continuous inspection process. The practice of the invention is equally appropriate for batch processes, even though the benefits of on-line correction are reduced to a batch-wise correction. Although not being bound by theory, it is believed that when the surface is heated it emits infrared radiation in a particular pattern as it cools. The surface travels between sensors 204, 206, 208 and 210. These sensors may be line scan IR cameras, CCD IR cameras which image defined fields, or the like, so long as they have the capability of capturing the pattern of heat radiating from the surface of the alloy. Sensors 204 and 210 detect the reflected heat, while sensors 206 and 208 detect the transmitted heat.

Suitable cameras include infrared two dimensional arrays such as the ThermaCAM SC1000™ camera manufactured by Inframetrics, Inc., North Billerica, Mass.; the Prisim DS™ camera, manufactured by FLIR Systems, Inc., Portland, Oreg.; and the Radiance™ camera, manufactured by Raytheon Amber, Inc., Goleta, Calif.

The heat radiating from the surface 202 changes over time as the surface travels in the direction of the arrow. The images captured by cameras 204 and 206 differ in time from those captured by cameras 208 and 210, therefore the pattern of cooling may yield additional information not found by a singular image. Image analysis software will differentiate between the cooling temperatures over time and deeper flaws will become visible or otherwise detectable.

Also to be carefully controlled is the speed of the surface being inspected, and the distance of the cameras from the heat source. Depending upon the thickness of the material and its thermal diffusivity, the thermal transient results in a change in the rate of temperature change. This "pulse" will reflect upon the rear surface of the material and return to the front surface as a secondary heat peak, i.e., change in rate of temperature change on the surface above the flaw. Such a peak will contain magnified information regarding flaws and the like which may be analyzed against the previous transmissive data to determine the precise location of flaws.

The images may be acquired to a database and displayed by appropriate software, e.g. EchoTherm™ Software, from Thermal Wave Imaging, Inc., Lathrup Village, Mich.; AnalyzIR™ Software from FLIR Systems, Portland, Oreg.; Dynamite™ real-time digital image storage software from Inframetrics, North Billerica, Mass.; or ImageDesk™ available from Raytheon Amber, Inc., Goleta, Calif.

Once a thermally acceptable image is established in an appropriate database, a neural network, e.g. Matlab™ Neural Network Toolbox™, fabricated by Math Works, Inc., Natick, Mass., or the Aegis Control™ Neural Network Software, fabricated by Neural Applications Corporation, Coralville, Iowa, which is capable of learning repetitive pattern imaging (image recognition) may analyze the recorded pulse for acceptability criterion.

Thus, optimally, the material will be traveling at a speed such that the first set of sensor cameras will image a transmissive thermal pulse, while the second pair of camera sensors will image an internally reflected thermal pulse, i.e., thermal signature.

Figure 3:
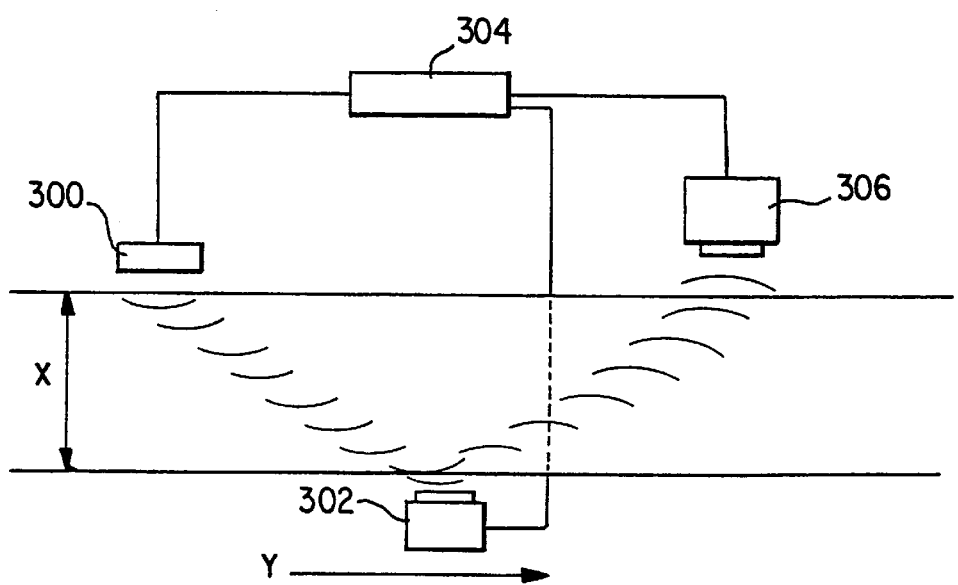
FIG. 3 is a side view of a material being inspected with transient thermal imaging according to the present invention.

FIG. 3 illustrates such a case. The thermal front is imparted by heat source 300 and travels as the material moves in the direction of single-headed arrow y. The thermal pulse travels through thickness x until it strikes the opposite surface in front of sensor camera 302 which records the thermal image emanating from the bottom of the material and sends it to controller 304. The wave is also partially reflected internally and travels back up to the upper surface, where it causes thermal emissions which are captured by sensor camera 306 and relayed to controller 304.

Various heat sources and types may be used—flash lamps can instantaneously raise the heating profile of the sheet being studied; lasers can scan the surface to provide a path of heating (diode lasers being preferred); conventional high intensity lamps (2000–8000 joules), preferably about 6000 joules; and magnetic induction coils may use the material as a susceptor to impart heat energy.

Figure 5:
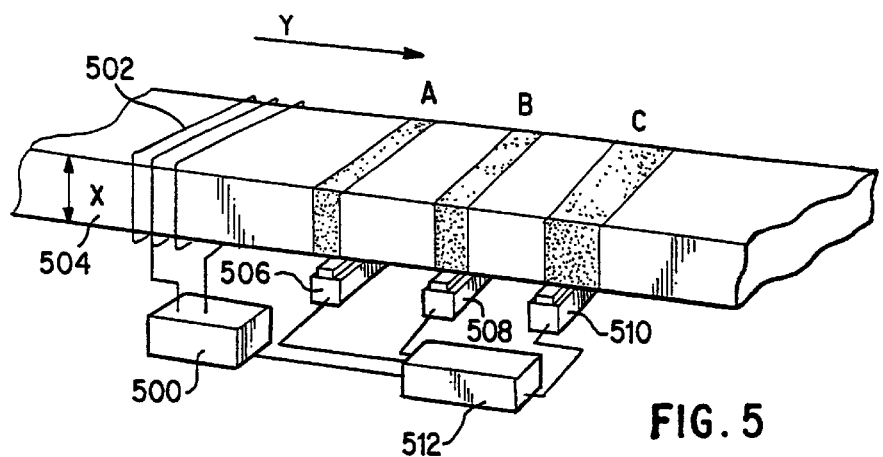
FIG. 5 is a perspective view of an inductively excited imaging system according to the present invention.

A magnetic induction heater for transient thermography is illustrated in FIG. 5. AC current source 500 powers induction coil 502. This imparts thermal energy to the material 504, provided it has sufficient metallic components which will function as a susceptor material to the expanding-contracting magnetic field generated by the induction coil. If the AC current is switched on and off it will create a transient thermal pulse within the material.

As the material travels in the direction of arrow y, the pulse conducts within the material and spreads out. Thermal band A is scanned by camera 506, while thermal band B is scanned by camera 508, and thermal band C is scanned by camera 510. The series of imparted thermal pulses is controlled by controller 512. The scanned images are also fed into controller 512 where they undergo image analysis to determine the presence or absence of flaws.

The novel inspection and control system of the present application has combined an effective thermal detection sensitivity with a predetermined stimulus impulse geometry and power profile to detect flaws, and consequently adjust the optimum system processing parameters for the manufacture of the sheet materials. Flaw location may also be "marked" to save on waste material, allowing for early removal of the material from the process control by excision by cutting. Excision may also consist of mere marking with a marker to indicate the material is not to be processed.

Figure 4:
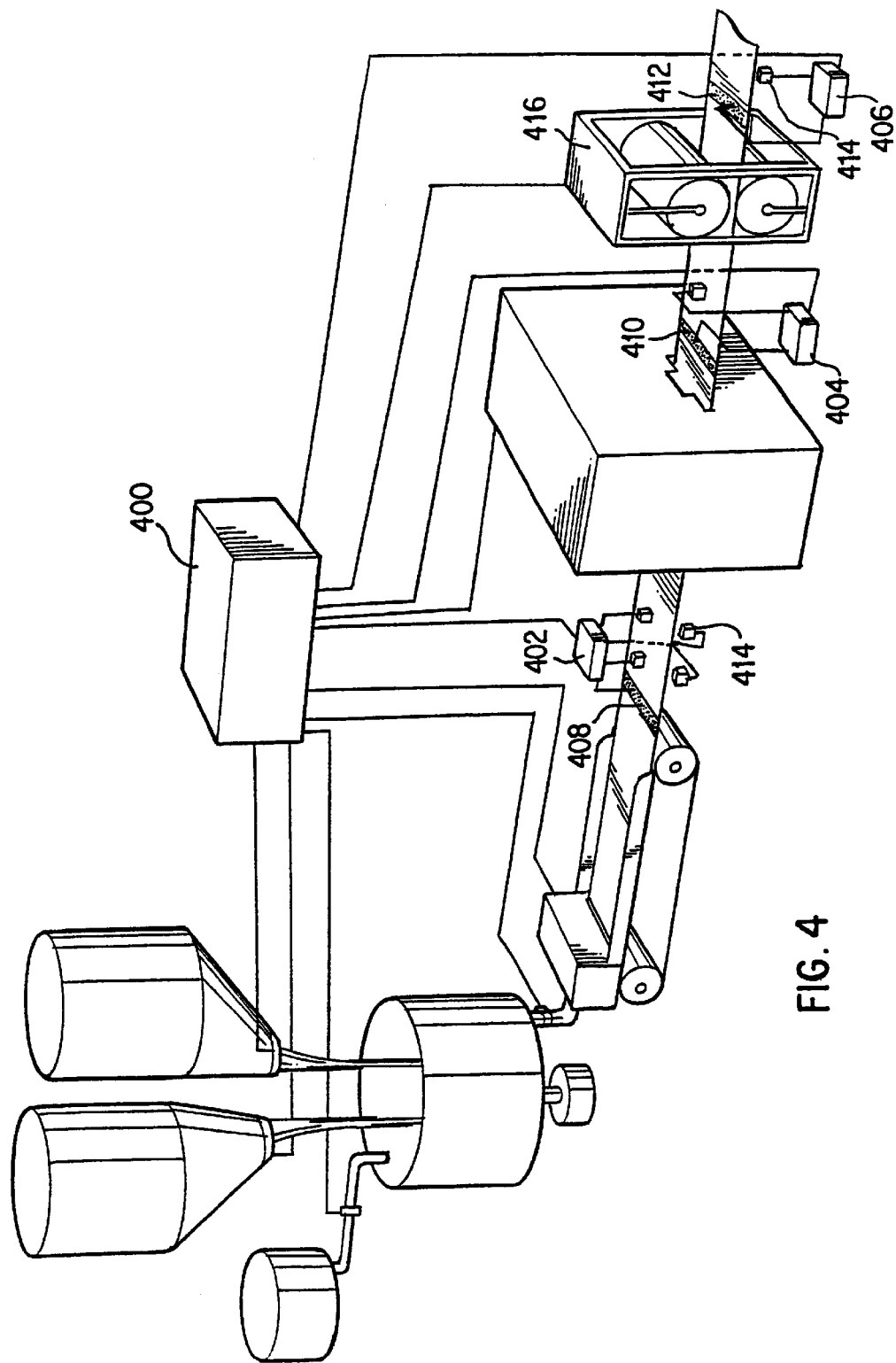
FIG. 4 is a perspective view of a production line for the manufacture of an alloy material according to the present invention with a preferred arrangement of inspection and feedback control.

Turning now to FIG. 4, it may be seen that such a system of inspection is placed in strategic locations in a manufacturing facility and integrated into the overall process control. Central controller 400 controls the overall functioning of the process, including regulating materials flow, thickness, speed of the conveyor, drying temperature, vacuum pressure and roller compaction pressure.

Inspection controllers 402, 404, and 406 are strategically placed immediately after various processing steps. Each inspection station is equipped with a respective heating means 408, 410, 412 for imparting a thermal pulse or thermal energy. The inspection stations then have paired or singular camera sensors 414 for inspecting the surface of the material.

Importantly, each of the inspection controllers is linked to the central controller and provides image analysis feedback to the controller. For example, if controller 412 indicates the density is right, but the thickness is wrong, the pressure on roll compactor 416 may be adjusted, and/or the orifice of the head box where the tape casting is extruded onto the conveyor adjusted to increase or decrease the thickness while maintaining the density.

Once the material has been excited thermally, several physics principles come into play. First, the thermal response of the material is a function of the thickness of the material. Second, the thermal response of the material is a function of its thermal diffusivity. Third, the thermal diffusivity of the material is affected by its constituent makeup and physical characteristics. Variations in local thermal properties can now be spatially correlated to defects such as cracks, inclusions, voids, disbonds, and other interruptions of uniformity.

An important part of the present invention includes the identification and calculation of appropriate relationships when dealing with thermal impulse In a materials environment, the thermal transient time under impulse heating is calculated by the following known equation:

$$k\nabla^2 T = \rho C \partial T / \partial t \qquad (I)$$

where $\rho$=density; k=thermal conductivity, T=temperature, and C=specific heat.

This holds true for the heat transfer of an isotropic homogeneous material.

This thermal transient time, of this material derives, in part, from the thermal diffusivity ($\alpha$), which is represented by the following:

$$\alpha = \frac{k}{\rho C} \qquad (II)$$

These relationships may be relied upon to predict a thermal field. Variations from this solution may be used to determine variations in the underlying material.

As we are interested in calculating the peak thermal impulse arrival time as a function of the thickness of the material being analyzed, we define it as the time for the arrival of the peak arrive at depth x. The second peak arrives when the reflected thermally diffused wave arrives at such depth point x. This reflection is from the back wall of the sample.

The techniques of transmissive and reflective thermography yield a key theoretical result, namely the relationship:

$$t_C \propto \frac{L^2 \rho C}{k} \qquad (III)$$

indicating that characteristic time constants ($t_c$) are fundamentally related (proportional) to sheet properties of thickness (L), density, thermal conductivity, and specific heat.

Establishing baseline values of each for the "ideal" product of manufacture in a database lookup table, or through preset gate values, enables a process central controller to determine when the values have strayed from the ideal and to manipulate an aspect of the production process, or a plurality of aspects of the production process to bring the values into acceptable limits. Such a database is established through a plurality of runs and subsequent analysis, but will be dependent on the material being processed and its desired parameters.

Figure 6A:
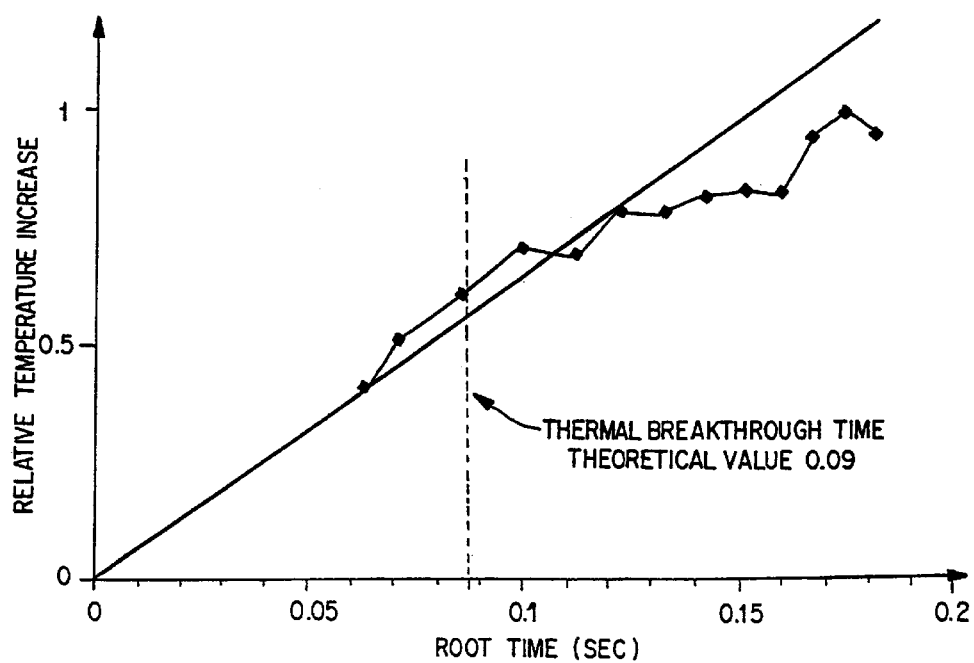
FIG. 6A is a graphical representation of the relative thermal increase versus the square root of time (root time)

FIG. 6A graphically illustrates the concepts discussed above. For a material being analyzed by thermal transmission, the surface scanned relative to temperature increase can be predicted based upon the calculated theoretical thermal breakthrough time. Variances from that plot indicate irregularities.

Figure 6B:
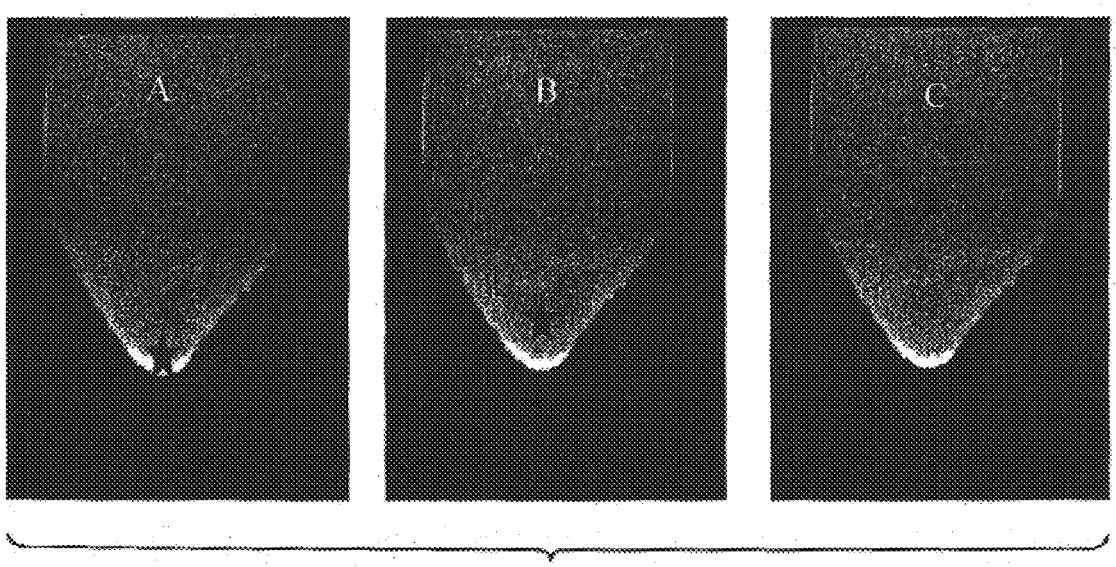
FIG. 6B is a triplicate image of a transmission imaged sample showing various sampling locations.

A specific case is illustrated in FIG. 6B, where a tapered sample of an iron aluminide green sheet having a thickness ranging from 0.013 inch to 0.026 inch was heated on the opposite side of the image collection device (thermal transmissivity). In the image designated A, the sampling location is almost at the tip; in the image designated B the sampling location is further towards the interior, and in the image designated C, the sampling location is central.

Figure 6C:
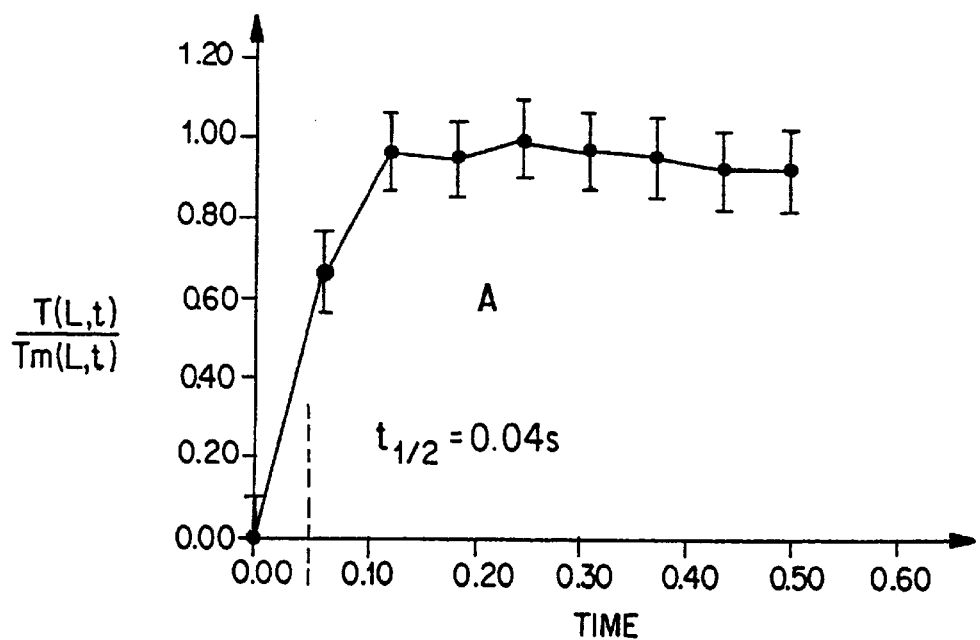
FIG. 6C is a graphical representation of the relative temperature change as a function of time at position A of FIG. 6B.
Figure 6D:
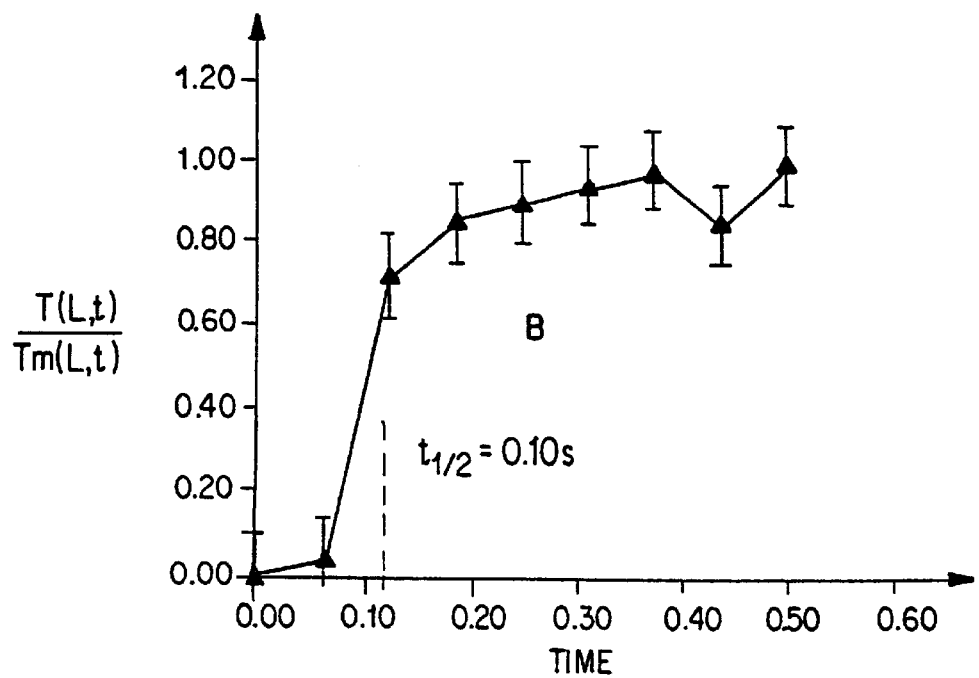
FIG. 6D is a graphical representation of the relative temperature change as a function of time at position B of FIG. 6B.
Figure 6E:
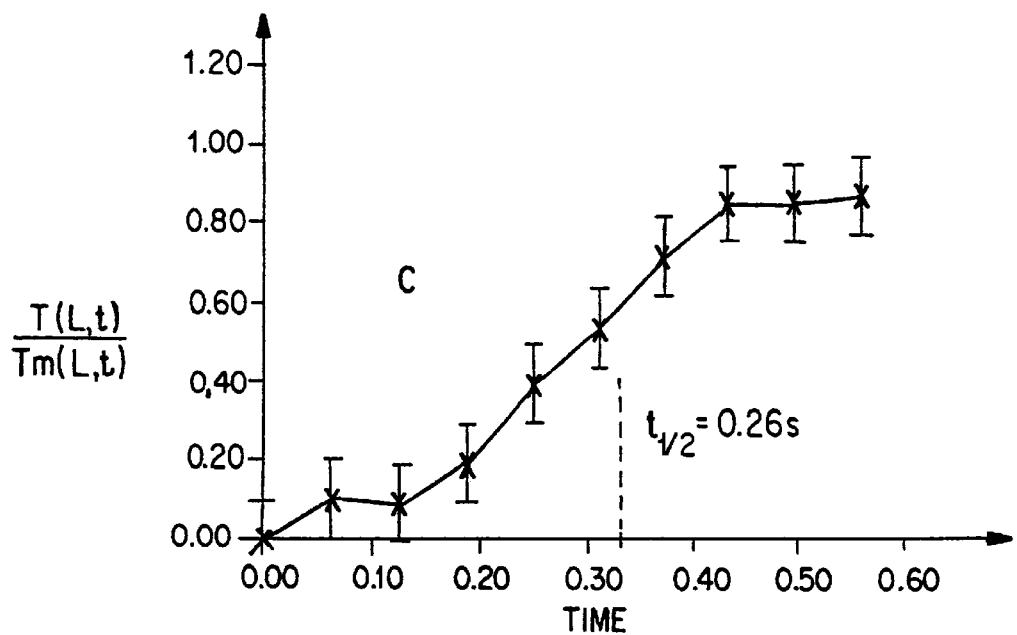
FIG. 6E is a graphical representation of the relative temperature change as a function of time at position C of FIG. 6B.

Turning now to FIGS. 6C, 6D, and 6E, plotted as a function of time (x axis) versus instantaneous temperature, characteristic curves are developed. Plainly, A differs from B which differs from C. Data analysis will tell one exactly how. For example, the $t_{1/2}$ times may be quantified as A=0.04, B=0.10, and C=0.26, which may be directly correlated to thickness, density, specific heat, and thermal conductivity. As may be seen from equation III, once three parameters are known, the last may be calculated and compared to the independently measured value.

In an especially preferred embodiment, a 6 kilojoule flashlamp is used as the illumination source. The camera is set to a line scan instead of full frame scan, allowing for a 12 kHz scan time with 30 lines being scanned.

Figure 6F:
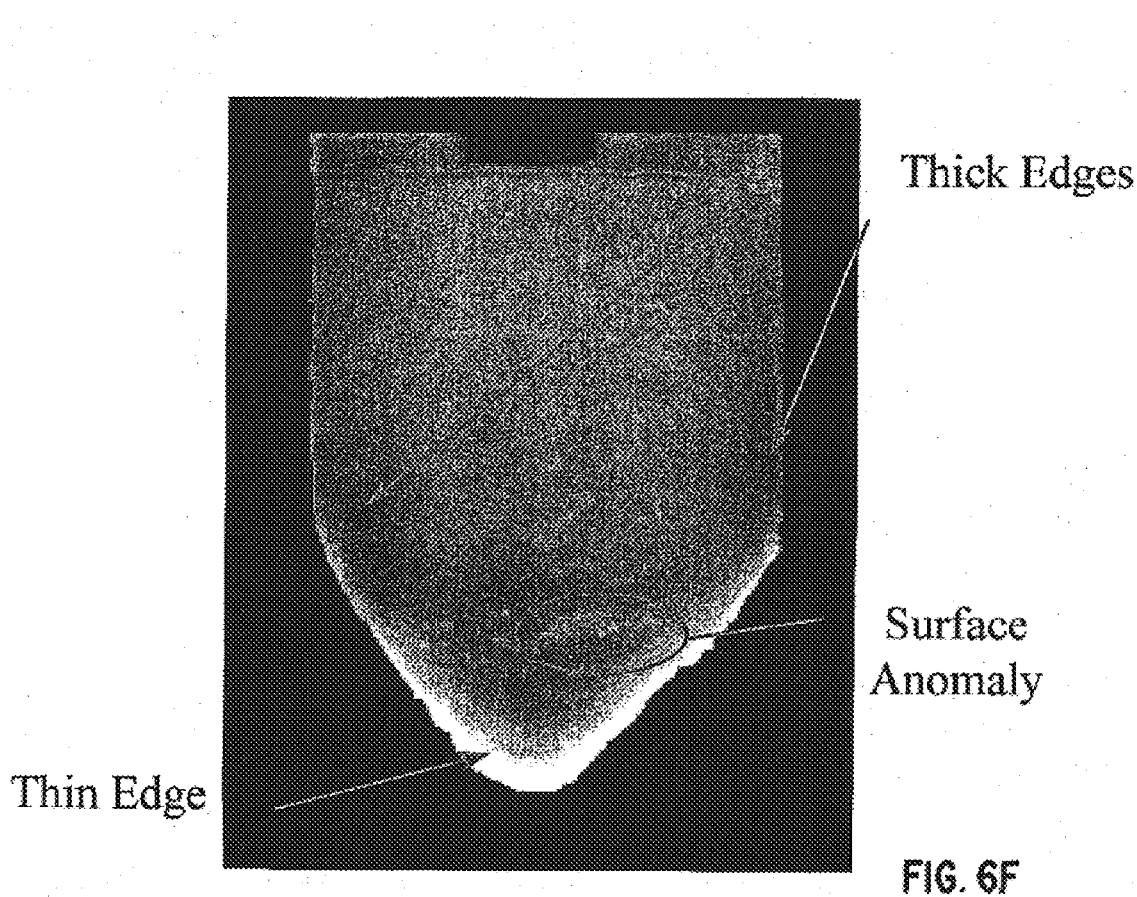
FIG. 6F is a reflectance image according to the present invention.

Given space considerations in processing plants, a preferred embodiment of the present invention has all of the imaging equipment on a single side of the material being analyzed. FIG. 6F illustrates such an image obtained by external reflective imaging, 0.167 seconds after step heating, where the heat is being constantly applied. Flaws become readily apparent.

One embodiment of the present invention which increases its data collection ability is as follows. One surface (usually the upper) is bombarded with high intensity photons beginning at a very precise point. The shadow, i.e. the delay time it takes for the wave front to get to the other surface provides a very accurate measurement of the thickness of the sample being analyzed. Simultaneously, immediately thereafter, or in parallel, thermal pulses from another source may be imparted to measure density and inspect for flaws. The simultaneous acquisition of both data pieces enables the density and thickness to be calculated separately.

Figure 7:
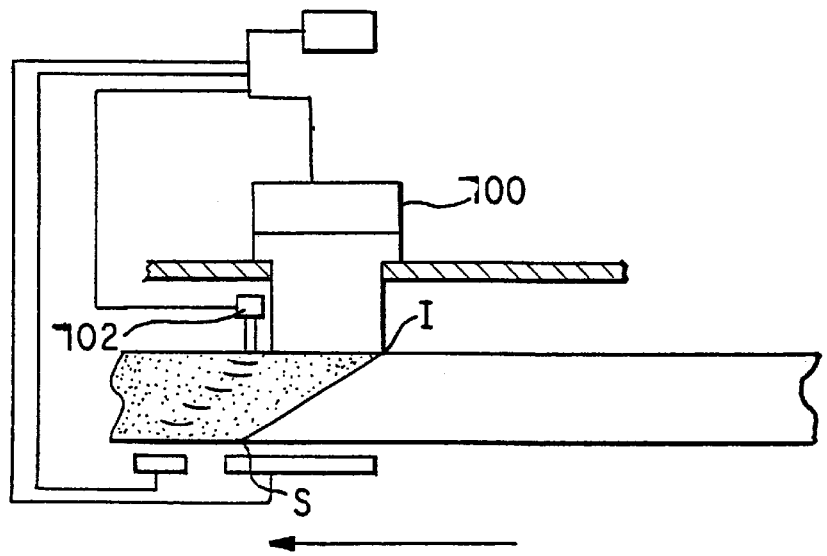
FIG. 7 is a side view of a preferred embodiment of the thermal imaging system of the present invention.

Turning now to FIG. 7, the dual inspection system of the preferred embodiment of the present invention is illustrated. A photonic or other illumination source 700 impinges upon the surface of the material at point I. The "shadow" effect of the material causes a delay in the radiation travel to point S. The duration of this travel, and the manner in which the wave arrives gives important analytical data as to the density, uniformity, and thickness of the material. It also establishes a baseline through which thermal impulses from second illumination source 702 travel. The data may then be statistically analyzed to separate out the density and thickness data.

Suitable instrumentation for receiving the thermal images from the surface of the material and associated equipment include the THERMOPROFILE© 6 LT Infrared Line Scanner, available from Agema Infrared Systems, Inc.

Figure 8:
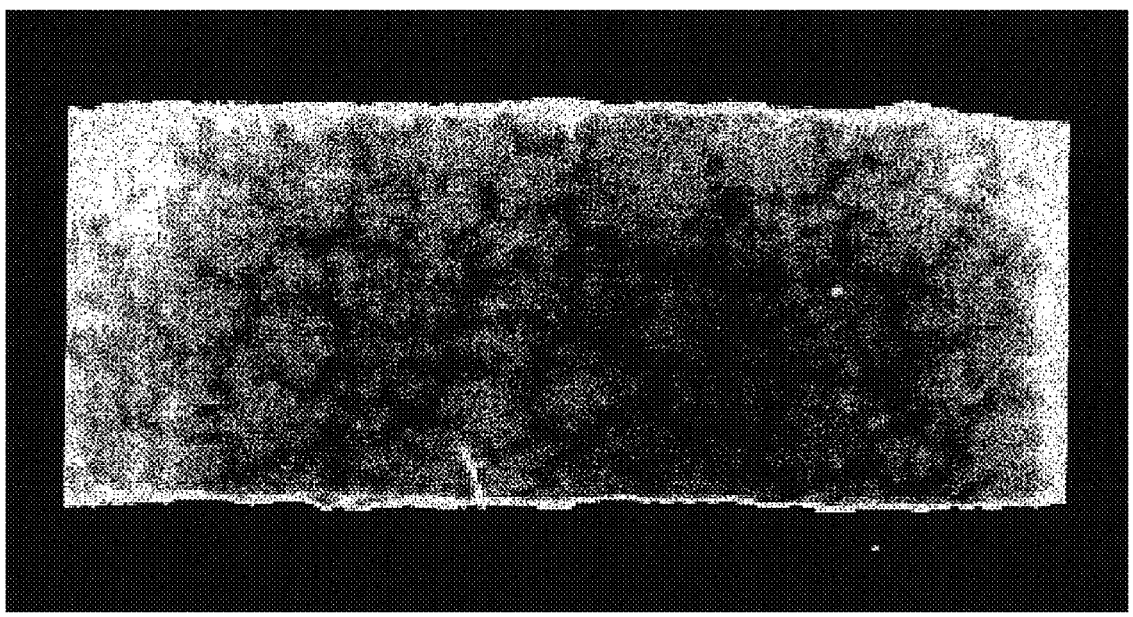
FIG. 8 is a reflectance image (of a tape cast sample) according to the present invention.

FIG. 8 is a digital image of a tape cast sample 0.010 seconds after a front flash. The loose structure is clearly visible with denser regions surrounded by cracks.

Figure 9A:
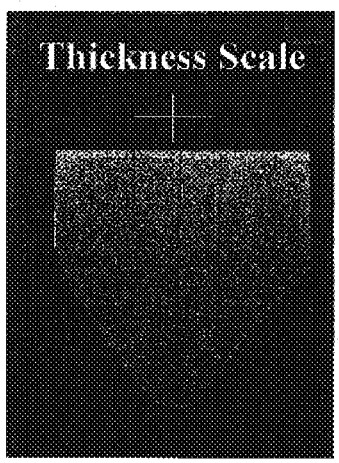
FIGS. 9A, 9B and 9C are digital illustrations comparing optical data (FIG. 9A shows an optical image from a digital camera), thermal data (FIG. 9B shows front surface heating), and physical measurement data (FIG. 9C shows representation of measurement data)
Figure 9B:
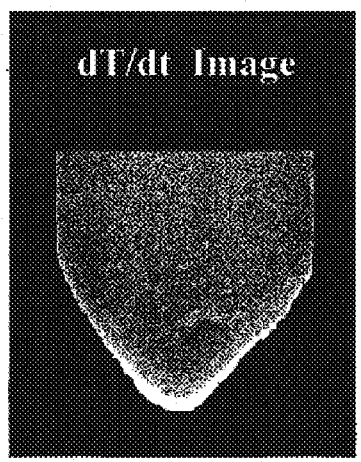
Figure 9C:
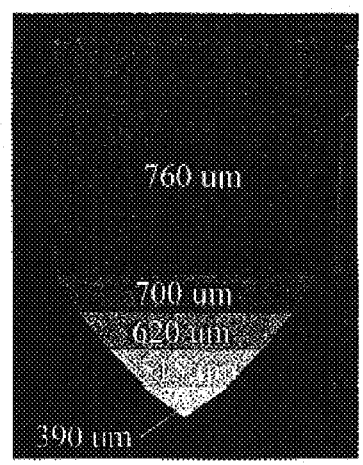
Figure 10A:
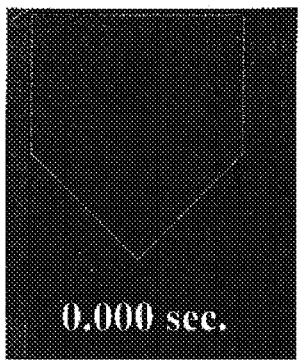
FIGS. 10A, 10B, 10C, 10D and 10E are digital images of, in time sequence, of thermal transmissive images according to the present invention.
Figure 10B:
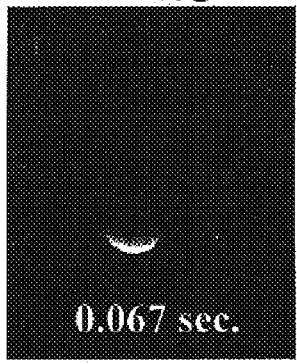
Figure 10C:
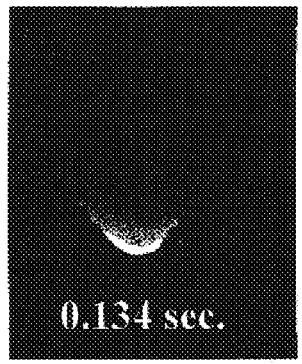
Figure 10D:
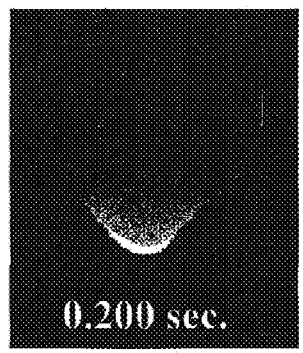
Figure 10E:
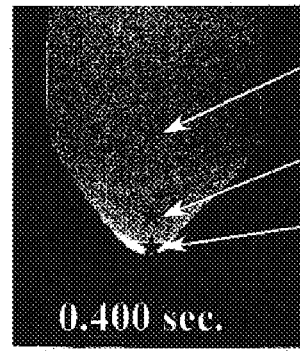

FIG. 9 compares an optical inspection with a transient thermography image and a physical measurement of the specimen. The thermography image glows brighter in the thinner regions where the photon flux from the surface is greater than the remainder of the sample.

FIG. 10 is an example of transmittal thermography illustrating a time lapse series of images where a tapered sample becomes clearly evident. The thinnest portions become visible in a faster manner, and they remain brighter for a period of time.

Figure 11:
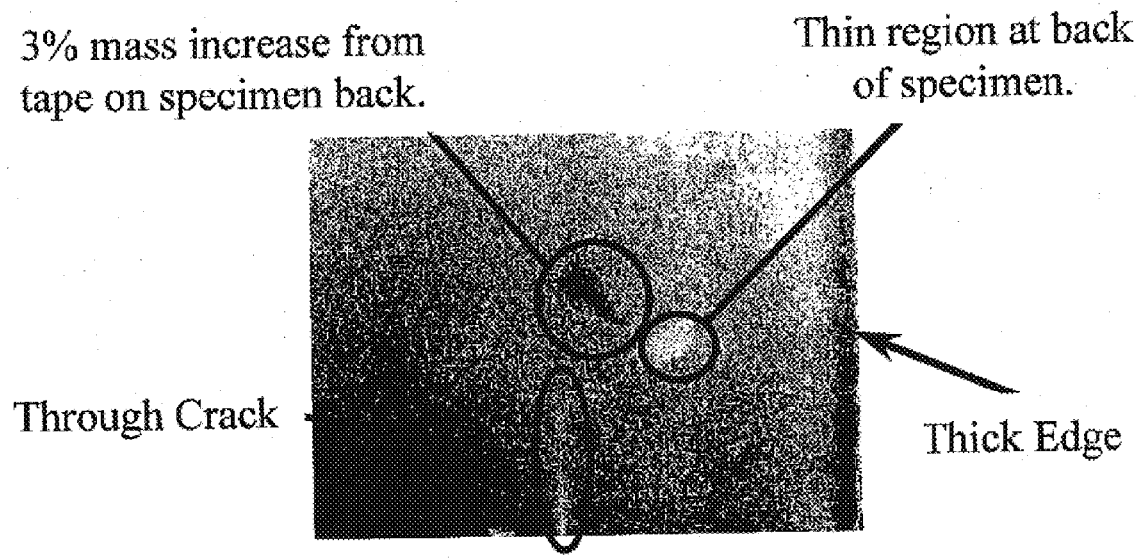
FIG. 11 is a digital image of a sample-containing defects, imaged by reflectance according to the present invention.

FIG. 11 is an example of transient thermography's ability to spot a multitude of defects, including excess mass, thin regions, cracks, and edge deformities.

In a preferred embodiment, the defect region is registered and identified for removal from the process flow. It may be marked automatically with a visible indicator, or the process controller may register and automatically remove the production portion from the stream by physical excision.

This invention is especially preferred for sheet material having a thickness dimension much smaller than its width or length, wherein for purposes of the sample and diffusion, it is essentially one dimensional.

According to a second embodiment of the invention, an apparatus and method are provided for the detection, location, and quantitative characterization of defects in powder metal parts. According to this embodiment, part assessment can be provided on a time scale allowing for interactive process control and/or identification of defective material in batch or continuously produced material.

Many powder metal processes include a "green part" forming step which involves the shaping of powder parts. The parts may be simple in shape or very complex and may be obtained using compaction, injection molding, die casting, or tape casting processes. The formed composites often include binders, lubricants, and/or other additives which facilitate processing. Where necessary, the green part may then undergo a low temperature drying treatment to achieve the desired mechanical properties required for further processing. Final steps in the process may involve the elimination of non-metallic components and densification via sintering and/or applying pressure.

There are several manufacturing challenges characteristic of processes involving green parts. For instance, green and final part properties (e.g., strength, ductility, porosity, resistivity, etc.) and dimensions are dependent on the homogeneity (uniform mixing and void volume distribution) of the alloying constituents in the green state. In addition, many binder systems are sensitive to relative humidity, which influences the ability to form the green part. Once the viscosity of the green material exceeds a critical level, it is difficult and in most cases cost prohibitive to redistribute the mass distribution in green parts. The criticality of these properties/dimensions, with regard to part performance, varies with application. Heterogeneity in green parts can lead to failure during post-green material processing or, if the green material is successfully fabricated into a final part, premature failure during service.

The rapid quantitative measurement of key green part properties allows for intelligent quality management decisions to be made regarding green part disposition (i.e., continued processing, re-work, or discard) and process control strategies. For example, by monitoring the time radiance history of a thermally excited green part one can access the quality, future defect distribution, and dimensional variation within the sample. Various excitation modes (spatial and temporal), commercially available hardware for excitation, and infrared radiation detection sensors may be used.

The spatial variation of the thermal properties of the green composite provides important information about heterogeneity and moisture level which can yield flaws (cracks, porosity, etc.) in subsequent processing steps. A specific example is the use of thermal effusivity variations to detect green part flaw precursors. Thermal effusivity provides a quantitative measure of the thermal impedance of a region of material. It manifests itself as the square root of the product of the composites bulk density, specific heat, and thermal conductivity. When a same side flash/detect technique is used, the variation in detected signal depends on both the bulk material properties and the geometry. In addition, the details of the distribution of the composites components (e.g., metal particles, binders, voids) influences bulk properties and these component thermal interactions are of a complex nature.

According to the invention, it is possible to take into account the detailed contribution of material distribution, component concentration, and geometry on bulk thermal behavior. In contrast, were one to merely inspect the radiance history of a thermally excited green part, the detection of a variation in material geometry might be indistinguishable from a change in material property. According to the invention, developed relationships and standards are used to calibrate for flaw detection in green parts. These standards may be samples of known binder (as filler or lubricant) and powder metal combinations or standards based on green parts which performed satisfactorily under processing to yield conforming final parts.

The physical characteristics of green powder metal parts requires special consideration in developing appropriate high speed inspection techniques and methods. A non-contact technique is preferred since the material has low mechanical integrity. X-ray systems, on the other hand, do not provide the required high speed three-dimensional specimen data required. Ultrasonic techniques require a coupling medium which can damage green parts. Classical nondestructive electromagnetic techniques (e.g., eddy current) are slow and often require direct physical contact with samples. Commercially available equipment provides qualitative time resolved radiance data but such data depends on many variables and, alone, does not provide a conclusive indication of defects.

This invention provides a technique and apparatus for the detection, location, and quantitative characterization of flaws in powder metal green parts which are precursors to flaws in final parts. For example, in processing FeAl sheet, it is possible to significantly reduce the cost of manufacturing compacted FeAl sheet. The inspection technique according to the invention is intended to detect and locate critical green sheet flaws which would result in the generation of scrap in the subsequent roll compaction manufacturing process. Thus, the invention can provide a way to filter out flawed green sheet material and reduce the overall cost of fabricating fully processed FeAl sheet material. The flaw identification can be accomplished fast enough to provide feedback to manufacturing equipment and thereby improve manufacturing capabilities and reduction in amount of scrap green sheet. Another advantage is the ability to determine sheet thickness independent of composition. In contrast, X-ray attenuation over the specimen thickness does not allow for such an independent determination (i.e., density and thickness variation cannot be separated using a single beam-single position geometry).

Figure 12:
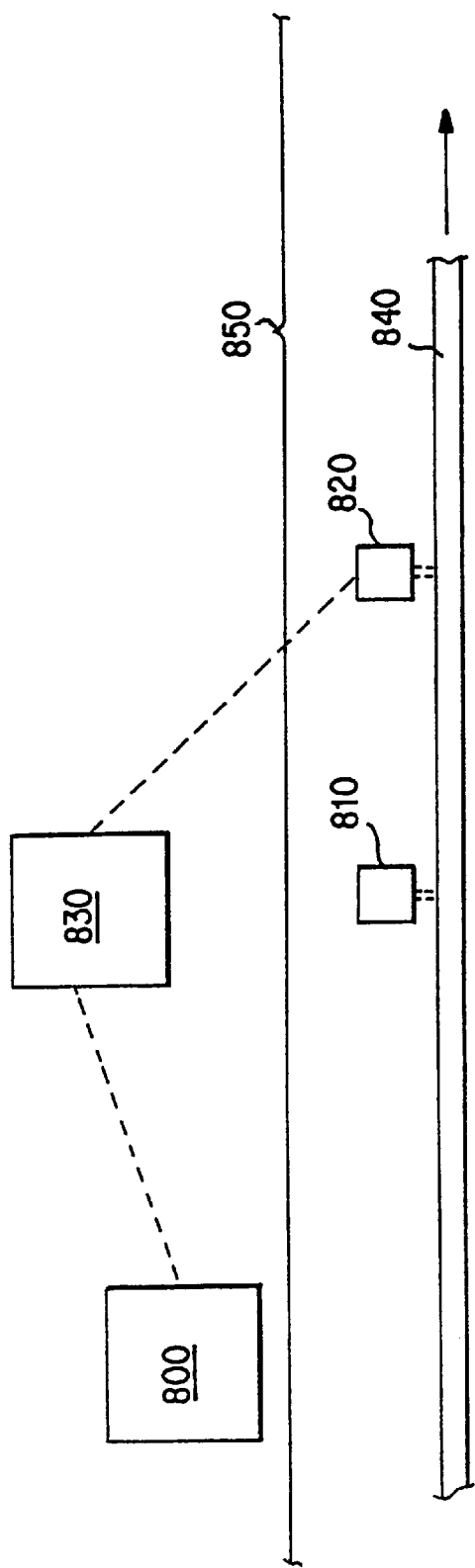
FIG. 12 illustrates an apparatus according to the invention wherein a thermal gradient initiator is used to heat or cool a continuously formed product of isotropic or non-isotropic material.

Details of the inspection technique according to the invention are now explained with reference to FIGS. 12–24. FIG. 12 illustrates an apparatus for controlling process variables in accordance with the second embodiment of the invention, the apparatus including a central process controller 800, a thermal gradient initiator 810, an infrared detector 820, and a computer 830. The central process controller 800 controls one or more process variables during manufacture of a product 840 in a manufacturing line 850. The thermal gradient initiator 810 heats or cools the product 840 at a location along the manufacturing line and the detector 820 receives a thermographic image or images such as by use of optical lenses and/or mirrors. The thermal gradient initiator can be an object such as a heat source or heat sink or a chemical reaction such as an exothermic or endothermic reaction in the product being produced. The computer receives and analyzes the image or images and determines one or more physical characteristics of the product. If the determined physical characteristic is outside a range of predetermined values, the central process controller modifies one or more of the process variables and/or records the location and/or size of flawed material in the product.

Figure 13:
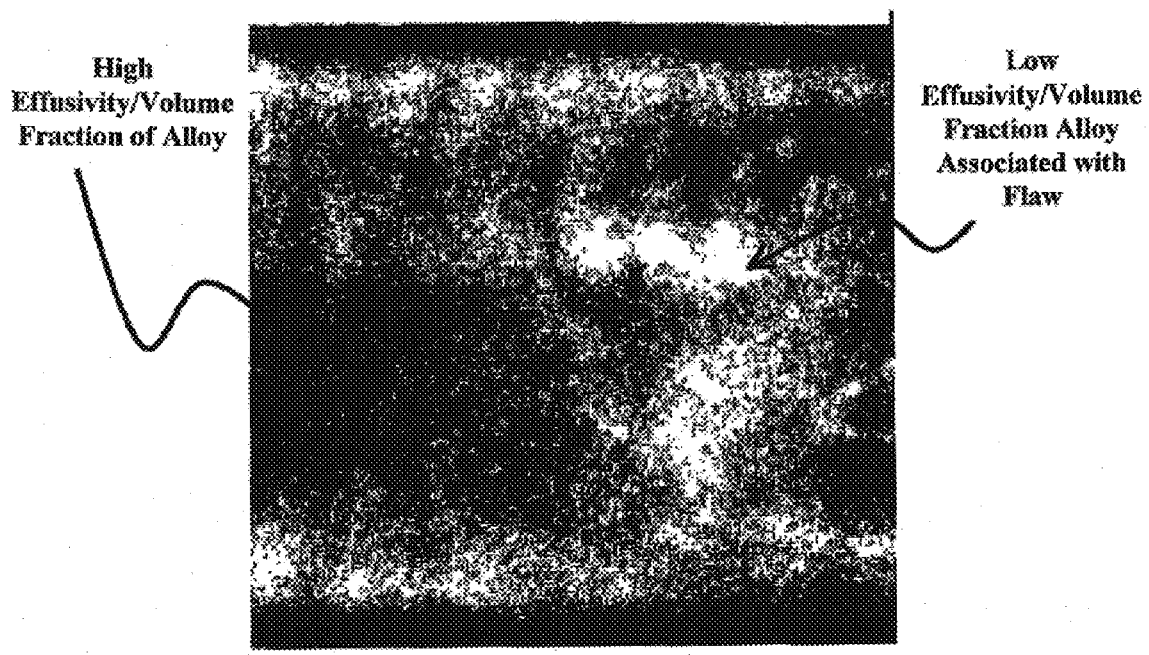
FIG. 13 illustrates a two dimensional map of the thermal effusivity for a sample of FeAl green sheet wherein the machine direction is to the left, the transverse direction is toward the bottom of the figure, and the flaw on the right side of the figure represents a crack and low density area.
Figure 14:
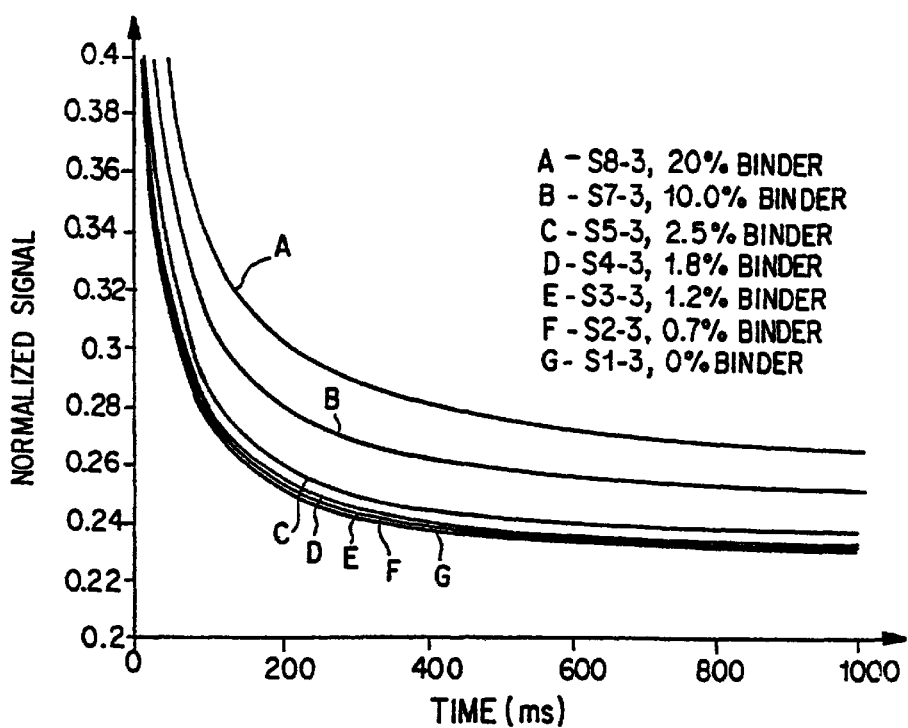
FIG. 14 shows a graph of signal vs. time for variation in binder and illustrates the time decay of surface temperature over regions of varying binder concentration in a sample of FeAl green sheet.

FIG. 13 illustrates a two dimensional map of the thermal effusivity for a sample of FeAl green sheet. The location at which a crack formed in a low density area during densification of the sheet is indicated by arrow A. FIG. 14 illustrates the time decay of surface temperature over regions of varying binder concentration. The difference in any two curves at early times, relative to the diffusion distance into the material, is indicative of the relative thermal effusivity. Slower decays are associated with lower thermal effusivity. It can be seen that the higher the binder concentration the lower the compacts thermal effusivity (i.e., higher binder concentrations result in higher thermal impedance). A similar effect is observed for void concentration. As shown by the bottom curve, at binder contents below about 3% there is not much change in the normalized signal.

Figure 15:
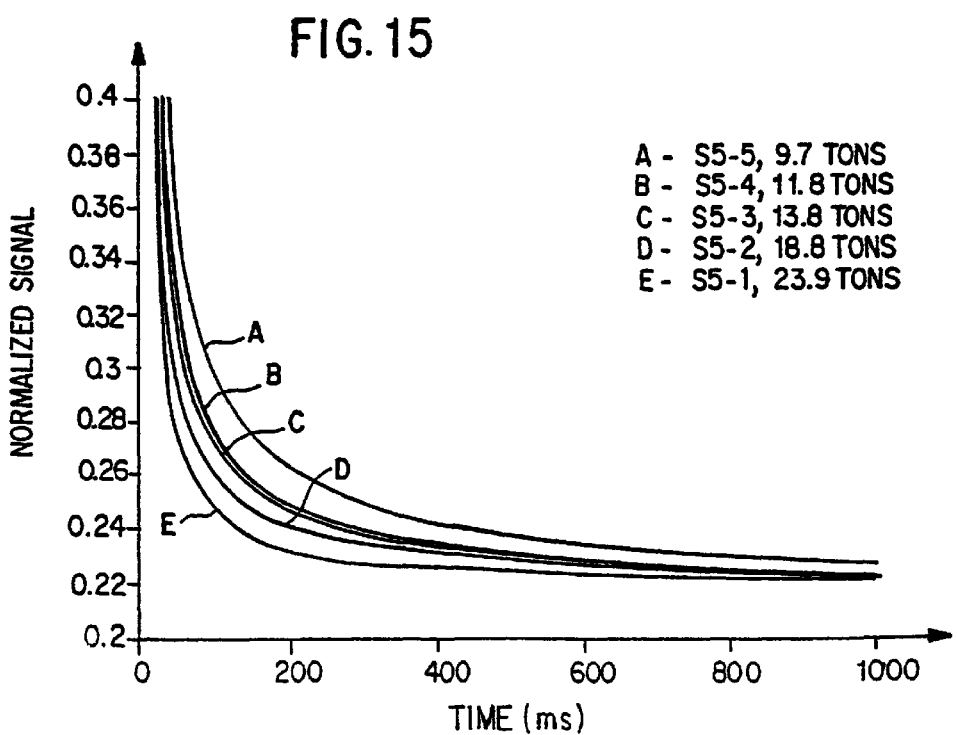
FIG. 15 shows a graph of normalized signal vs. time for variation in pressure and illustrates the time decay of surface temperature over FeAl samples with nominal binder concentration and varying compaction pressure.

FIG. 15 illustrates the time decay of surface temperature over samples with nominal binder concentration and varying pressure applied to the powder mixture which corresponds to compaction pressure in the case where the powder mixture is rolled. The difference in any two curves at early times, relative to the diffusion distance into the material, is indicative of differences in thermal effusivity. It can be seen that the lower the compaction pressures the lower the bulk effusivity (i.e., lower pressure results in higher thermal impedance). Both these effects result from the fact that the primary heat conduction route is via metal particle interaction. Thus, composite features which limit heat transfer between these particles, such as increased inter-particle distance or particle insulation via voids or binder, decrease the effusivity. It should be noted that since the amount of X-ray attenuating material (in this case metal powder) is constant, for all these samples, an X-ray scan would not indicate differences in these samples (i.e., X-rays cannot distinguish the fact that these samples were subjected to different process pressures).

Figure 16:
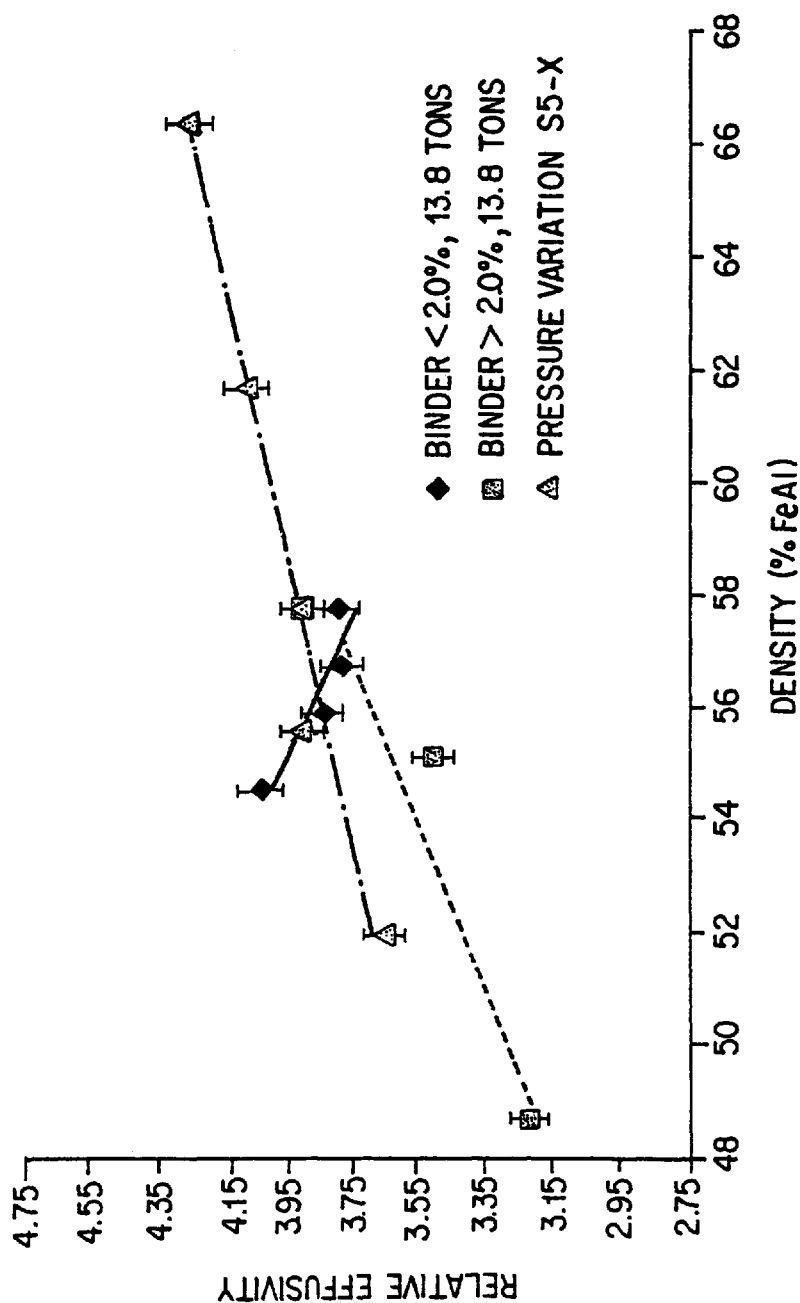
FIG. 16 shows a graph of effusivity vs. %FeAl density and combines results of FIGS. 14 and 15 by showing how the green compact's relative effusivity varies with composition and pressure.

FIG. 16 combines results of FIGS. 14 and 15 and shows that the green compact's relative effusivity varies with composition and pressure. The results are surprising in that the trend of increasing density with increasing relative effusivity for FeAl having over 2% binder is reversed in the 54 to 58% density range for FeAl having less than 2% binder. The reason for this surprising result is that as the binder increases to about 3% the binder lubricates the metal particles and enhances thermal transport between the particles. However, above about 3% binder, the interparticle spacing becomes large enough to cause a decrease in density of the powder mixture. Thus, there is a density peak at around 3% binder. The effects of inhomogeneous binder content are manifested by low green strength with too little binder and the potential for voids which form during rolling with high but nonuniform binder contents. Such voids can lead to lack of particle bonding during sintering of the green material.

Figure 17:
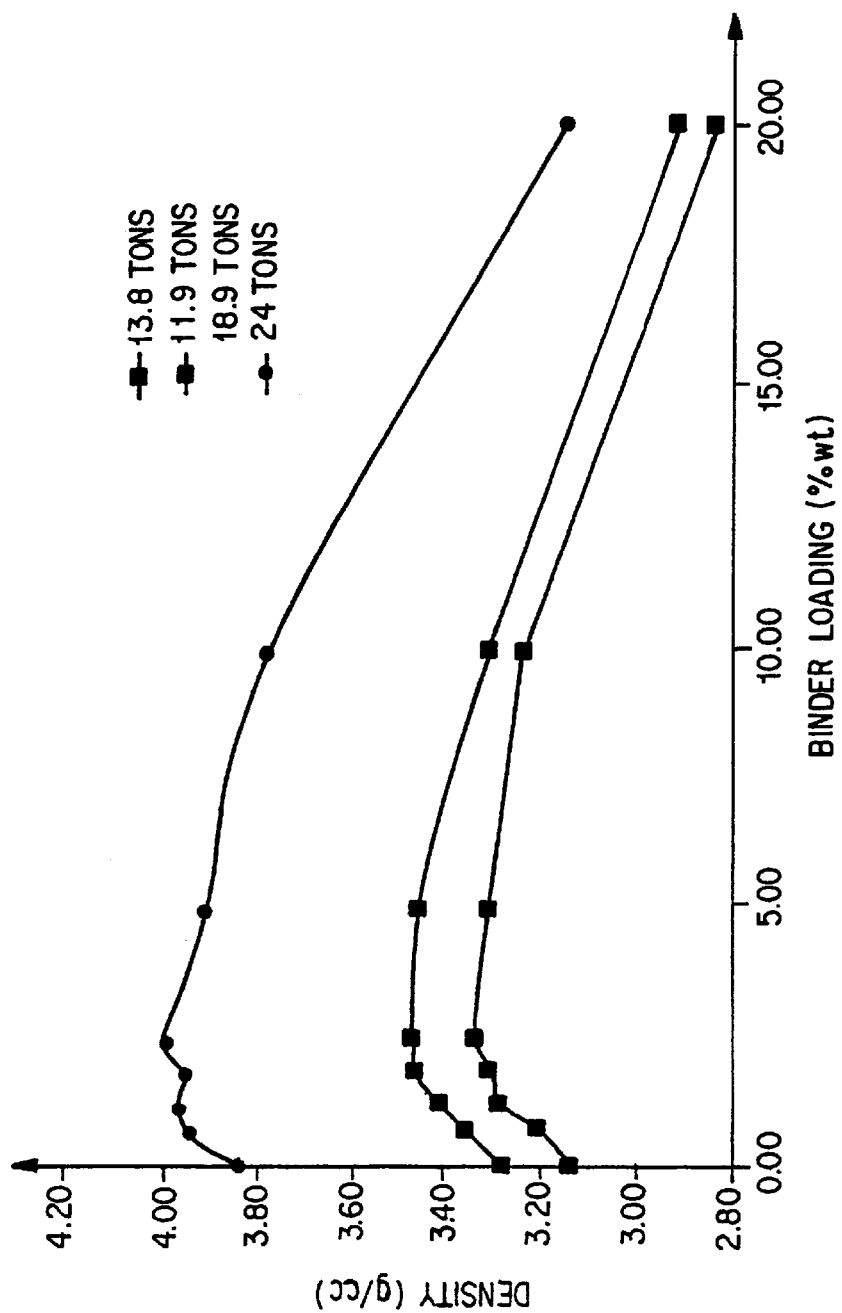
FIG. 17 shows a graph of density vs. binder loading and illustrates the non-trivial dependence of compact density and binder loading.
Figure 18:
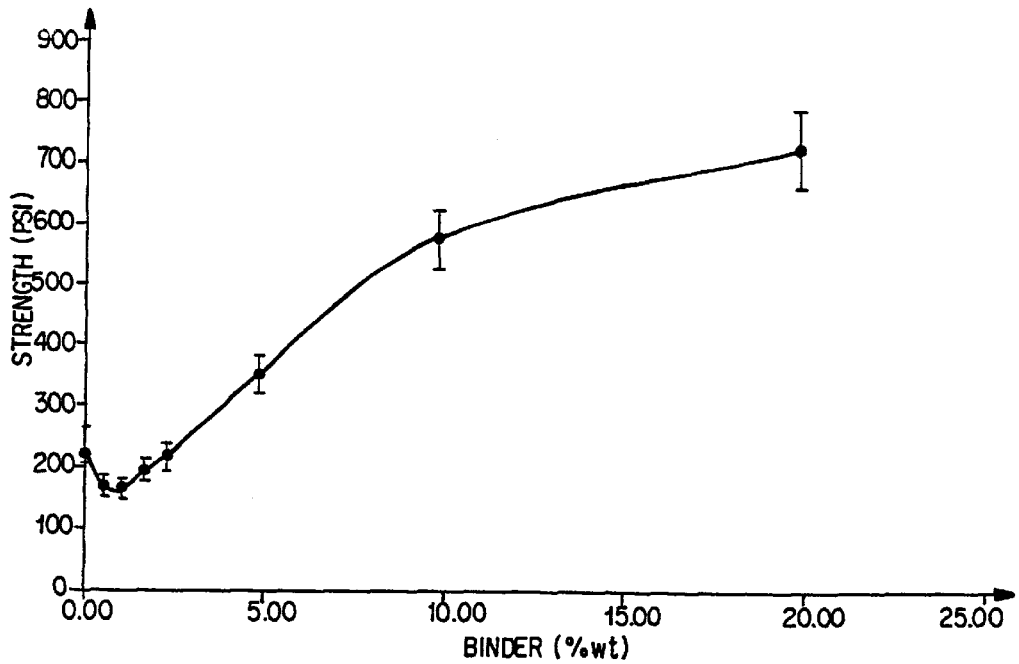
FIG. 18 shows a graph of strength vs. binder
Figure 19:
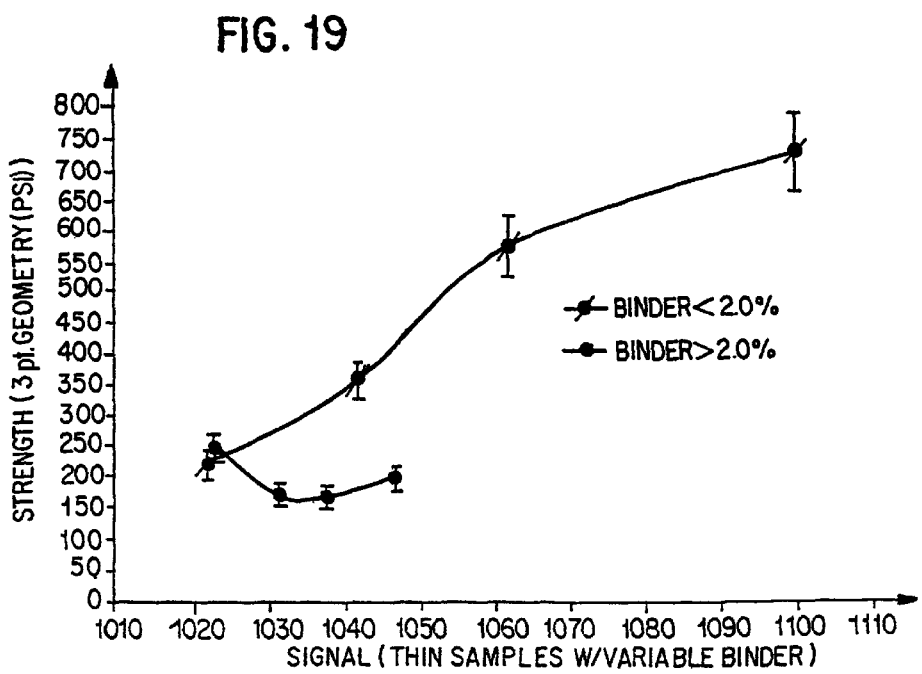
FIG. 19 shows a graph of strength vs. signal (@168 ms), each figure illustrating strength versus binder curves for FeAl green sheet.

FIG. 17 illustrates the non-trivial dependence of green density and binder loading. This results in the complex strength versus binder curve illustrated in FIG. 18. As shown in these curves, the green strength decreases with an increase in binder content up to about 3% binder after which the green strength increases with incresing binder content. FIG. 19 shows that the green strength can be predicted (above a certain binder threshold) based on the relative radiance signal (inversely proportional to the effusivity). A green strength above a minimum level is necessary for the handling of green parts.

Figure 20:
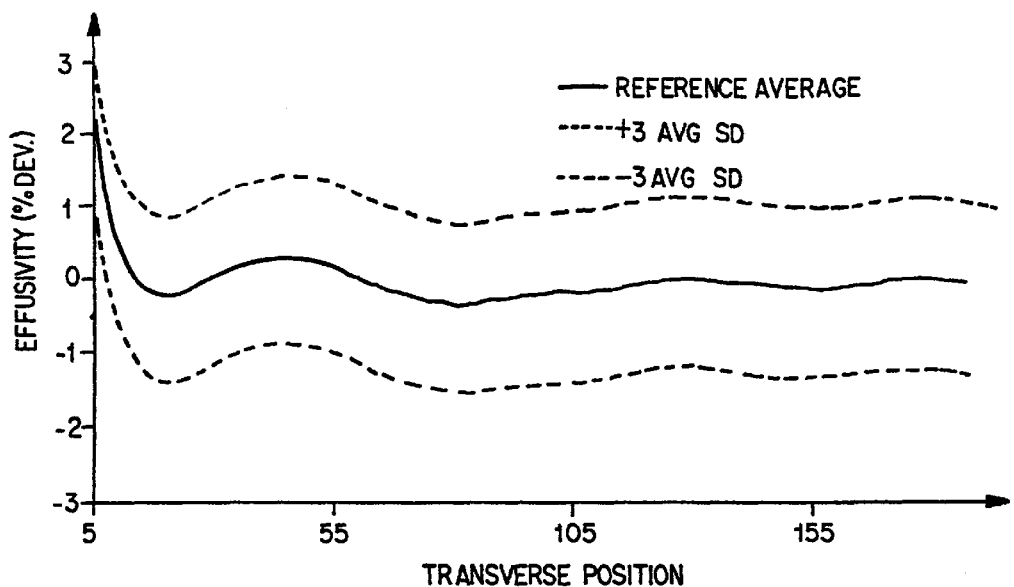
FIG. 20 shows a graph of effusivity vs. transverse direction (reference averaged over machine direction) and illustrates the effusivity variation in reference green sheet (sheet which survived processing to yield acceptable fully dense FeAl sheet)

FIG. 20 illustrates the effusivity variation in reference green sheet (sheet which survived processing to yield acceptable fully dense FeAl sheet). The transverse direction is transverse to the sheet rolling direction (in this case down the page of FIG. 13). Similar graphs can be made for the orthogonal direction. The variation in the spatial derivative of the effusivity can thus be obtained for reference green sheet. It is both absolute heterogeneity and the spatial gradient of such heterogeneity which results in flaws. Again, the data can be processed in a similar manner for the orthogonal direction. Gradient maps (analogues to the effusivity map of FIG. 13) can also be generated using matrix filters.

Figure 21:
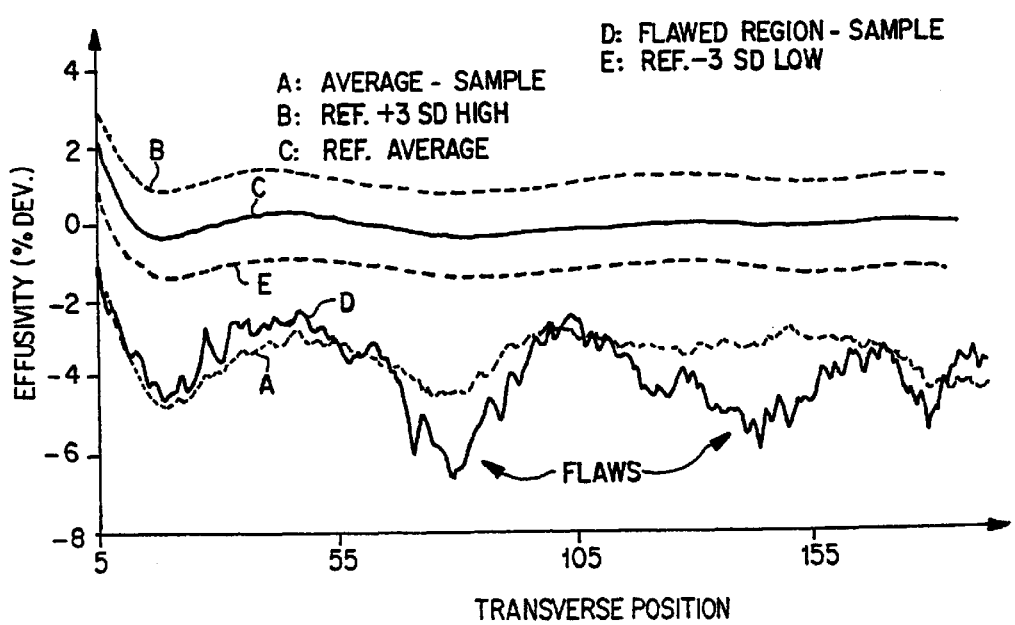
FIGS. 21 and 22 show graphs of effusivity vs. transverse direction (averaged over machine direction 41-frm3, pos 0) and illustrate the deviation of the effusivity (of the material represented in FIG. 13) with respect to the reference material.
Figure 22:
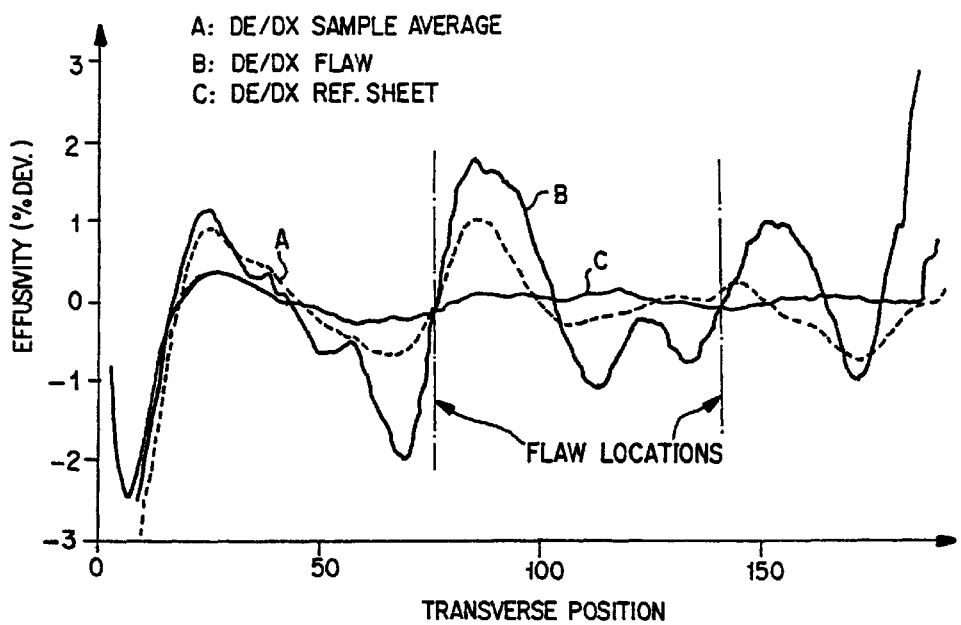

FIGS. 21 and 22 illustrate the deviation of the effusivity (of the material represented in FIG. 13) with respect to the reference material. The first sign of the presence of a flaw is that the average is outside the range of the reference curve. Secondly, large gradients and spikes in effusivity occur in regions for which high porosity and cracking occurred. The location of the resulting crack was predicted using the zero crossing of the derivative curve as shown in FIG. 22.

Figure 23:
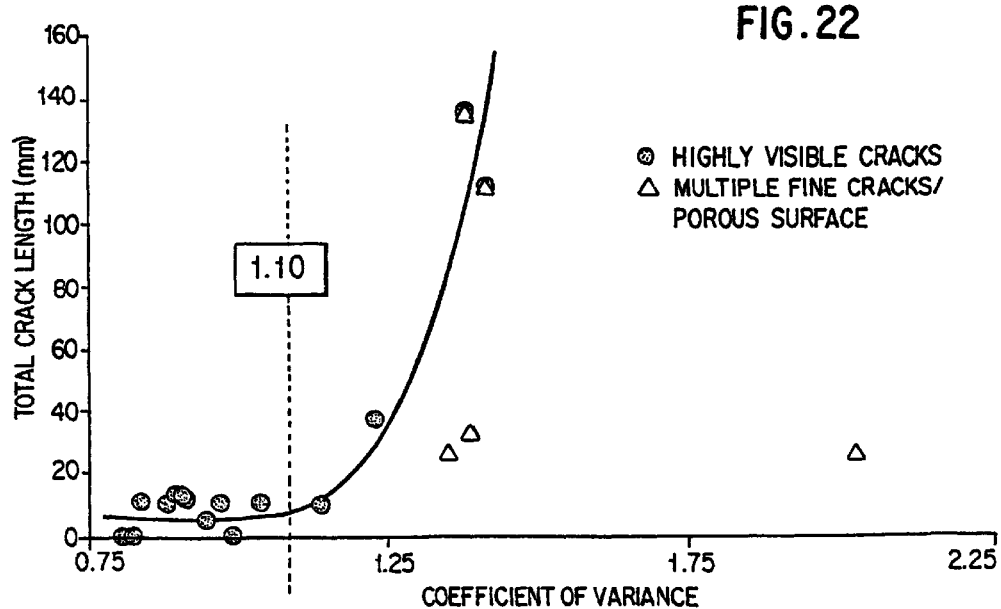
FIG. 23 shows a graph of green sheet homogeneity as a predictor of FeAl crack formation and illustrates the ability to predict the frequency of crack formation in dense FeAl sheet by determining the starting green sheet heterogeneity.

FIG. 23 illustrates a statistical approach for predicting the frequency of crack formation in dense FeAl sheet by determining the starting green sheet heterogeneity. The deviation from a purely homogeneous material is determined from the statistical spread in effusivity over the green sheet volume. The presented data is based on the processing of 30 feet of green sheet. When the coefficient of variance of the green sheet effusivity exceeds a threshold of about 1.10 the total crack length for highly visible cracks generated during subsequent processing (i.e., the summation of the length of all cracks generated in the production of fully dense FeAl sheet) increases sharply. Within the powder metal industry, an index of mixture homogeneity (ranging from 0 to 1) is typically determined from sampling compact properties. If desired, the variation in effusivity could be cast in the same form. Densified sheets, which exhibited undesired porosity, also fall in the region above the threshold. Both of these defects (cracks and porosity) result from green sheet with locally low levels of metal powder concentration. The degree of heterogeneity is useful for screening purposes. When detailed knowledge of flaw severity and location is demanded, the analysis described above is required.

According to the invention it is possible to combine early decay information with late decay data to determine sample thickness independent of sample composition. The early data (e.g., data corresponding to bulk properties such as density, thermal conductivity and specific heat) provides a direct measure of effusivity "e" which is defined as $e=(k\rho C)^{1/2}$. This can be obtained using standards of known composition (see earlier discussion regarding FIG. 14). At much later times the thermal diffusion length exceeds that of the thickness of the sample and a change in cooling rate occurs (see earlier discussion regarding Equation III). The time of this change varies as the square of the thickness. By using the early time data to identify the appropriate composition reference cooling curve for a half space, the thermal breakthrough time (change in cooling rate) can be determined and actual thickness determined. Accordingly, one could use the early time data to obtain sample composition and use the sample composition data and later time data to determine sample thickness.

The detection technique according to the invention is now described with reference to the production of a continuous non-metallic product such as tobacco. In particular, according to this embodiment, a technique is provided wherein it is possible to measure characteristics associated with variations in mass distribution, deviation from flatness, moisture level and other process parameters associated with the manufacture of tobacco containing sheet material. These characteristics can be measured off-line or on-line and the results incorporated into a process feedback control strategy. The tobacco material may be a film formed product, a product which is wet cast onto a substrate, a dry application process, or a product made in a paper making process. The product may also be the result of a process combining all or any of the above forming techniques.

The physical measurement includes scanning the surface of the sheet using an infrared detector and the associated optics (infrared radiometry). The data obtained depicts the apparent temperature field of the sheet. This information can be stored and processed using appropriate image processing hardware and software as discussed previously. Once relevant correlations between the sheet fabrication process variables and features of the apparent thermal field have been determined, image processing algorithms (known to or derivable by those skilled in the art) can be used to monitor the process. In other words, using the techniques discussed above with reference to making powder metal products, thermal properties and heterogeneity can be assessed to determine quality of other materials such as tobacco containing material.

The apparent thermal distribution of the temperature field depends on the spatial distribution of the various materials used in the sheet. Taking into account that even under isothermal conditions different materials may be detected due to differences in emissivity giving rise to different apparent temperatures, it is possible to use the apparent thermal distribution to detect differences in local moisture content and differences in local mass concentration. All of these factors can result in differences in heat transfer to the sheet. The result is a variation in the time for thermal diffusion through the sheet. Thermal gradients in the sheet may be induced as part of the process (e.g., as the result of a drying process) and/or by an active element such as a heating lamp or heated surface over which the sheet is passed. For example, the heat transfer between a sheet and a supporting surface such as a drum or belt can provide a heat flux into or out of the sheet depending on the temperature differential of the sheet surface and the support surface.

The variations in heat transfer throughout the sheet are influenced by, among other factors, the variations in physical separation of the sheet surface and the support surface. As a result, areas of the sheet in intimate contact with the support will be at an elevated temperature (for the case of heat flux into the sheet) when compared to regions in which there is a significant separation between the two surfaces. This allows for topological information to be obtained from the apparent thermal field. The complex topography of such a sheet can be related to the types of influences mentioned above. Thus, the statistics of the topography may be related to the changes in macroscopic properties within the sheet and ultimately related to bulk performance characteristics of the sheet such as strength, flexibility, etc.

The apparent thermal field can be used to indicate heat transfer between a heated surface and various different tobacco sheet materials. For instance, thermal effusivity can be measured using an arrangement wherein a heated surface is used to supply heat to a sheet of tobacco and an IR camera with associated optics, image processing hardware and software receives an IR image reflected off of a mirror. The heated surface can be at about 50° C. and differential heat flow can be measured by the camera whereby the resulting heat intensity profile field can be used to indicate changes in mass distribution and flatness of the sheet material. Deposits of dry tobacco separated by a gap from areas of wet cast tobacco may show up on an infrared thermograph as light areas showing the presence of a carbon mat with a wet cast of tobacco thereon and dark areas showing the presence of a carbon mat having dry tobacco thereon. An infrared thermograph may also include dark areas indicating where material has been displaced up and away from the substrate and light areas indicating regions where material is in close contact with the substrate. Thus, light and dark areas of an infrared thermograph can be used to detect variations in flatness of the material.

According to this embodiment, it is possible to monitor, in real time, important characteristics of a sheet material. The technique can be used to inspect a tobacco sheet material or any sheet of other material such as paper which contains no tobacco. Techniques, such as infrared spectral absorption for the determination of moisture content and optical inspection techniques (i.e., those which operate in the visible region of the spectrum) for the inspection of surface designs by reflected light or the determination of path length by attenuated transmitted light, do not provide for the measurement of sheet heat transfer properties of such a sheet while in a manufacturing process. Knowledge of sheet heat transfer properties, however, provides information on the variations of mass distribution within the sheet, sheet topography, as well as total sheet mass content. Using current state of the art hardware and software, it is possible to provide data acquisition rates which are fast enough to incorporate the information obtained with this technique into a process control strategy and thereby improve the consistency of manufacture products with respect to features such as thickness, flatness, composition, moisture level, etc. Thus, the present embodiment provides a technique for real time feedback control of various products such as processed tobacco or paper wherein detection of differential in-plane variations in heat flow can provide data concerning changes in mass distribution and flatness to a process controller. The process controller, in turn, can utilize software and/or hardware to adjust process variables to minimize sheet properties (such as mass distribution, flatness, etc.) falling outside a desired process window.

The invention is now explained with reference to an embodiment wherein the detection, location, and quantitative characterization of defects in tobacco composite material are used to provide an assessment on a time scale allowing for interactive process control. The technique is useful for monitoring and modifying process control in making tobacco materials and composites (e.g., cast leaf, coated mat, etc.) designed to have specific mass/constituent distributions, mechanical properties and dimensions. Examples of constituents of such tobacco products include tobacco particles, tobacco paper products, and glycerin. The fraction of each constituent and the state of the intermediate products (e.g., mat prior to coating at a particular moisture content and temperature) result in intermediate materials which have unique properties critical to achieving the final product specification. In some cases, as in the case of coated mat, specific anisotropic properties such as strength are desired while for other applications such as FeAl sheet isotropic properties may be desired. There are several challenges posed in the manufacturing and inspection of these materials. One is the rate at which the material is fabricated. For instance, coated mat is produced at many square meters per minute whereas flaws which impact performance can be as small as a few square centimeters. Techniques which use a beam to sample the mass under various regions of the sheet are limited to sampling small fractions of the material and thus are not sensitive to the spatial distribution (e.g., homogeneity along the beam path). According to the invention it is possible to obtain rapid quantitative measurement of key tobacco material/composite properties. This allows for intelligent operator or automation based quality management decisions to be made regarding material disposition (i.e., continued processing, recycling or discard) and process control strategies.

According to the invention, the time radiance history of a thermally excited material composite part is monitored and used to assess the quality future defect distribution, and dimensional variation within the sample. The monitoring can be carried out using various excitation modes (spatial and temporal), commercially available hardware for excitation and infrared radiation detection sensors. For example, the spatial variation of the thermal properties of the material can be used to provide information about heterogeneity and moisture level which can lead to flaws (e.g., porosity, etc.) in subsequent processing steps. A specific example is the use of thermal effusivity variations to detect flaw precursors. As discussed earlier, the thermal effusivity provides a quantitative measure of the thermal impedance of a region of material and is manifested as the square root of the product of the composites bulk density, specific heat and thermal conductivity.

Figure 24:
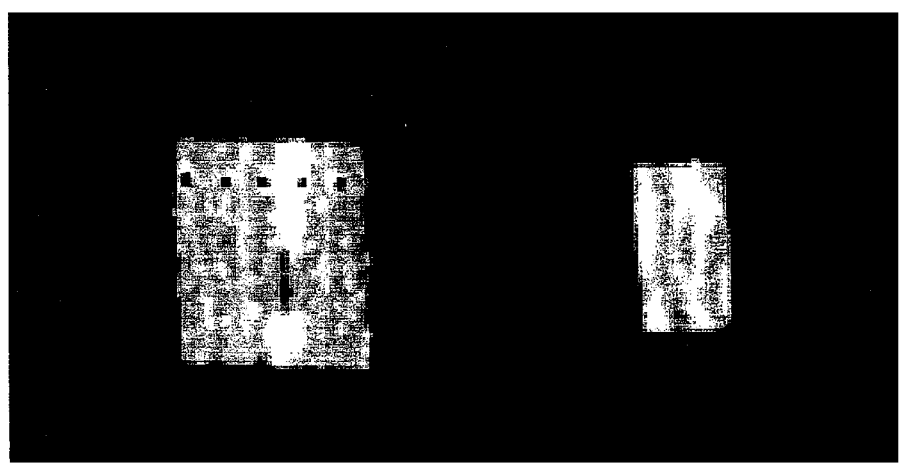
FIG. 24 shows a thermograph of a tobacco composite having a layer of adhesive, a mat and a coating of tobacco, the image on the left having a coating weight of 205 g/m$^2$, 10.5% gly and perforated holes and wherein two light areas correspond to the mat alone and a dark area corresponds to the adhesive and mat and coating and the image on the right having a coating weight of 170 g/m$^2$ and 9% gly.

The images in FIG. 24 illustrates the difference in thermal impedance of different coated mat composite sheets. The highest scale value (white) is indicative of high thermal impedance while lower scale values (darker) are associated with low thermal impedance. The black background is a thick steel plate. The composite on the left has a sheet weight specification of 205 $g/m^2$ and the composite on the right has a sheet weight specification of 170 $g/m^2$. Note that along a vertical region of sample on the left (high loading) a glue anchor line has been pealed partially away. The result is that one region in the image (the dark spot) consists of substrate plus coating plus adhesive. This region exhibits the lowest thermal impedance from both samples. Along the same vertical line (above and below) the removal of the adhesive also removed the coating from the substrate. The substrate alone exhibits the highest impedance. Note that in the coated regions, the higher loaded sample has a lower impedance (darker) than the sample with the lower coating level (lighter).

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. An apparatus for inspecting a sheet material produced by a production process having a process flow, comprising:
    a central process controller configured to control at least one aspect of the production process;
    a source of incident radiation which impinges upon the sheet material;
    a conveyor for moving the sheet material in a single plane;
    at least one infrared detector located proximate to a surface of the sheet material, said infrared detector positioned such that it can create an image of the surface of the sheet material at or downstream of the source of incident radiation; and
    a computer which is in communication with the central process controller and configured to receive and analyze the image from the infrared detector to determine physical characteristics of the sheet material, and transmit the determined physical characteristics to the central process controller, so that the central process controller adjusts the at least one aspect of the production process in response to the determined physical characteristic, wherein the infrared detector outputs early time data and later time data corresponding to a time decaying image of the sheet material, and the computer determines a first physical characteristic of the sheet material on the basis of the early time data, and a second physical characteristic of the sheet material on the basis of the first physical characteristic and the later time data.

2. An apparatus as claimed in claim 1, further comprising an index device for locating an inspected portion of the sheet material.

3. An apparatus as claimed in claim 1, further comprising an excisor to remove an inspected portion of the sheet material from the process flow.

4. An apparatus as claimed in claim 1, wherein there are a plurality of sources of incident radiation impinging on the same location, at least one of which is pulsed.

5. An apparatus as claimed in claim 4, wherein there are at least as many infrared detectors as radiation sources.

6. An apparatus as claimed in claim 1, wherein there is an infrared detector positioned to receive the externally reflected radiation.

7. An apparatus as claimed in claim 1, wherein there is an infrared detector positioned to receive the internally reflected radiation.

8. An apparatus as claimed in claim 1, wherein there is an infrared detector positioned to receive transmitted radiation.

9. An apparatus as claimed in claim 1, wherein the source of incident radiation is a lamp generating light selected from the group consisting of visible light, infrared light, and ultraviolet light.

10. An apparatus as claimed in claim 1, wherein the source of incident radiation is inductive.

11. An apparatus as claimed in claim 1, wherein the source of incident radiation is a laser.

12. An apparatus as claimed in claim 1, wherein the source of incident radiation puts out between 2,000 and 8,000 joules.

13. An apparatus as claimed in claim 1, wherein the source of incident radiation puts out about 6,000 joules.

14. An apparatus as claimed in claim 1, wherein there are a plurality of cameras positioned downstream from the source of incident radiation, and the sheet material is translated at such a rate as to give time differentiated images of the same portion of the surface imaged in each camera.

15. An apparatus for inspecting a sheet material produced by a production process having a process flow, comprising:
    a central process controller configured to control at least one aspect of the production process;
    a plurality of sources of incident radiation which impinge upon the sheet material;
    a conveyor for moving the sheet material in a single plane;
    a plurality of infrared detectors located proximate to a surface of the sheet material, the infrared detectors positioned to create an image of the surface of the sheet material at or downstream of the sources of incident radiation, an infrared detector being positioned to receive transmitted pulsed radiation, and an infrared detector being positioned to receive transmitted unpulsed radiation; and
    a computer in communication with the central process controller and configured to receive and analyze the image from the infrared detectors to determine physical characteristics of the sheet material, and to transmit the determined physical characteristics to the central process controller, so that the central process controller adjusts the at least one aspect of the production process in response to the determined physical characteristic.

16. An apparatus as claimed in claim 15, wherein the infrared detectors generate data which is compared to separate density and thickness information.

17. An apparatus for inspecting a sheet material produced by a production process, comprising:
    a source of incident radiation which impinges upon the sheet material;
    a conveyor for moving the sheet material in a single plane;
    a plurality of infrared detectors located proximate to a surface of the sheet material, each of the infrared detectors positioned downstream from the source of incident radiation and operable to create an image of the surface of the sheet material, the infrared detectors including an infrared detector positioned to receive transmitted pulsed radiation, and an infrared detector positioned to receive transmitted unpulsed radiation; and
    a computer which is in communication with the infrared detectors and configured to receive and analyze the images from the infrared detectors to determine physical characteristics of the sheet material, and transmit the determined physical characteristics to a controller.

18. An apparatus for inspecting a sheet material produced by a production process, comprising:
    a central process controller configured to control at least one aspect of the production process;

a plurality of sources of incident radiation which impinge upon the sheet material, at least one of which is pulsed;

a conveyor for moving the sheet material in a single plane at a predetermined speed;

a plurality of infrared detectors located proximate to a surface of the sheet material, the infrared detectors positioned such that they are downstream from the sources of incident radiation and can create images of the surface of the sheet material, the infrared detectors including an infrared detector positioned to receive transmitted pulsed radiation, and an infrared detector positioned to receive transmitted unpulsed radiation; and a computer which is in communication with the central process controller and configured to receive and analyze the images from the infrared detectors to determine physical characteristics of the sheet material, and transmit the determined physical characteristics to the central process controller so that the central process controller adjusts the at least one aspect of he production process in response to the determined physical characteristic.

19. A method of determining at least one characteristic of a sheet material produced in a continuous process, comprising:

bombarding the sheet material with incident radiation from a continuous source and a pulsed source of radiation;

translating the sheet material in a single plane at a predetermined speed;

detecting infrared emissions from the sheet material from a plurality of infrared detectors, the detecting including positioning an infrared detector to receive transmitted pulsed radiation, and positioning an infrared detector to receive transmitted unpulsed radiation; and analyzing the received radiation to determine at least one characteristic selected from the group consisting of density and thickness.

20. A method of determining at least one characteristic of a sheet material produced in a continuous process, comprising:

bombarding the sheet material with incident radiation;

translating the sheet material in a single plane at a predetermined speed;

detecting infrared emissions from the sheet material from a plurality of infrared detectors including at least one detector positioned to receive reflected radiation, the detecting including positioning at least one infrared detector to receive transmitted pulsed radiation, and positioning at least one infrared detector to receive transmitted unpulsed radiation; and analyzing the received radiation to determine at least one characteristic selected from the group consisting of density and thickness.

21. A method as claimed in claim 20, wherein the reflected radiation is externally reflected radiation.

22. A method as claimed in claim 20, wherein the reflected radiation is internally reflected radiation.

23. A method as claimed in claim 20, wherein the analyzing comprises training a neural network to recognize acceptable thermal signatures.

24. An apparatus for improving product quality by controlling one or more process variables as a function of at least one product characteristic monitored during manufacture thereof, comprising:

a central process controller including hardware and/or software effective to control one or more process variables during manufacture of a product in a manufacturing line;

a thermal gradient initiator which provides a thermal gradient within the product at a location along the manufacturing line;

a plurality of infrared detectors positioned to receive a thermographic image of the product at or downstream of the thermal gradient initiator, the infrared detectors including an infrared detector positioned to receive transmitted pulsed radiation, and an infrared detector positioned to receive transmitted unpulsed radiation; and a computer including hardware and/or software to communicate with the central process controller, receive and analyze the image from the infrared detector, and determine at least one physical characteristic of the product, and output data corresponding to the determined physical characteristic to the central process controller, the central process controller modifying one or more of the process variables when the determined physical characteristic is outside a range of predetermined values for the physical characteristic.

25. An apparatus as claimed in claim 24, wherein the manufacturing line includes a forming station wherein the product is formed into a continuous length of particulate ceramic, metal or organic material, the central process controller being effective to vary composition and/or shape of the particulate material when the determined physical characteristic is outside a range of predetermined values for the physical characteristic.

26. An apparatus as claimed in claim 24, wherein the manufacturing line includes a heating station wherein the product is heated to an elevated temperature, the central process controller being effective to vary the elevated temperature to which the product is heated when the determined physical characteristic is outside a range of predetermined values for the physical characteristic.

27. An apparatus as claimed in claim 24, wherein the determined physical characteristic is measured at a plurality of locations along the manufacturing line.

28. An apparatus as claimed in claim 24, wherein the thermal gradient initiator comprises a substrate support on which the product is carried along the manufacturing line.

29. An apparatus as claimed in claim 24, wherein the thermal gradient initiator comprises a cooling device which provides the thermal gradient by cooling the product.

30. An apparatus as claimed in claim 24, wherein the infrared detector receives pulsed and/or unpulsed thermal radiation from the product.

31. An apparatus as claimed in claim 24, wherein the determined physical characteristic is at least one of density and thickness of the product.

32. An apparatus as claimed in claim 24, wherein the thermal gradient initiator comprises a lamp generating light selected from the group consisting of visible light, infrared light, and ultraviolet light.

33. An apparatus as claimed in claim 24, wherein the thermal gradient initiator comprises a device which heats the product by inductive, ultrasonic, microwave or laser heating.

34. An apparatus as claimed in claim 24, wherein the computer compares the received image to one or more reference thermographic images of a product having desired properties.

35. An apparatus as claimed in claim 24, wherein the manufacturing line includes a station at which particulate material is deposited on a conveyor belt and the controller regulates process variables including thickness of the particulate material deposited on the conveyor belt, amount of the particulate material deposited on the conveyor belt, and/or speed of the conveyor belt.

36. An apparatus as claimed in claim 24, wherein the manufacturing line includes a roll compaction station and/or a heating station, the controller being effective to regulate process variables including amount of pressure applied by rollers at the roll compaction station, thickness of the product exiting the roll compaction station, and/or temperature to which the product is heated in the heating station.

37. An apparatus as claimed in claim 24, wherein the manufacturing line includes a station at which a plurality of metal powders are blended together with a binder and subsequently deposited on a conveyor belt, the controller being effective to regulate process variables including degree of blending of the blended powders, homogeneity of the blended powders, composition of the blended powders, thickness of the blended powder deposited on the conveyor belt, amount of the blended powder deposited on the conveyor belt, and/or speed of the conveyor belt.

38. An apparatus as claimed in claim 24, wherein the thermal gradient initiator heats the product to a temperature no greater than 100° C. and the detector comprises a camera which has a pixel array, the pixel array generating decay curve data corresponding to a decay curve for each pixel of the pixel array, the computer being effective to analyze the decay curve data and determine if the determined physical characteristic is outside the range of predetermined values.

39. An apparatus as claimed in claim 24, wherein the thermal gradient initiator comprises an endothermic or exothermic chemical reaction in the product.

40. A method for improving product quality by controlling one or more process variables as a function of at least one product characteristic monitored during manufacture thereof, comprising:

controlling process variables in a process of manufacturing a product in a manufacturing line by a central process controller;

heating or cooling the product so as to provide a thermal gradient within the product at a first location along the manufacturing line;

using a plurality of infrared detectors to detect infrared radiation emitted from the product at or downstream of the first location and generating a thermographic image from the detected infrared radiation, including positioning at least one infrared detector to receive transmitted pulsed radiation, and positioning at least one infrared detector to receive transmitted unpulsed radiation;

using a computer to communicate with the central process controller, receive and analyze the image from the infrared detectors, and determine at least one physical characteristic of the product; and using the computer to output data corresponding to the determined physical characteristic to the central process controller such that the central process control modifies one or more of the process variables when the determined physical characteristic is outside a range of predetermined values for the physical characteristic.

41. A method as claimed in claim 40, wherein the manufacturing line includes a forming station wherein the product is formed into a continuous length of particulate ceramic, metal or organic material, the method including a step of using the central process controller to vary composition and/or shape of the particulate material when the determined physical characteristic is outside a range of predetermined values for the physical characteristic.

42. A method as claimed in claim 40, wherein the manufacturing line includes a heating station wherein the product is heated to an elevated temperature, the method including using the central process controller to vary the elevated temperature to which the product is heated when the determined physical characteristic is outside a range of predetermined values for the physical characteristic.

43. A method as claimed in claim 40, wherein the determined physical characteristic is measured at a plurality of locations along the manufacturing line.

44. A method as claimed in claim 40, wherein the thermal gradient is produced by heating or cooling the product using a substrate support on which the product is carried along the manufacturing line.

45. A method as claimed in claim 40, wherein the thermal gradient initiator comprises a cooling device which provides the thermal gradient by cooling the product.

46. A method as claimed in claim 40, wherein the method includes using the infrared detector to receive pulsed and/or unpulsed thermal radiation from the product.

47. A method as claimed in claim 40, wherein the physical characteristic determined by the computer is at least one of density and thickness of the product.

48. A method as claimed in claim 40, wherein the thermal gradient is produced by a lamp generating light selected from the group consisting of visible light, infrared light, and ultraviolet light.

49. A method as claimed in claim 40, wherein the thermal gradient is produced by inductive, ultrasonic, microwave or laser heating.

50. A method as claimed in claim 40, wherein the physical characteristic is determined by the comparing the received image to one or more reference thermographic images of a product having desired properties.

51. A method as claimed in claim 40, wherein the manufacturing line includes a station at which particulate material is deposited on a conveyor belt, the method including using the controller to regulate process variables including thickness of the particulate material deposited on the conveyor belt, amount of the particulate material deposited on the conveyor belt, and/or speed of the conveyor belt.

52. A method as claimed in claim 40, wherein the manufacturing line includes a roll compaction station and/or a heating station, the method including using the controller to regulate process variables including amount of pressure applied by rollers at the roll compaction station, thickness of the product exiting the roll compaction station, and/or temperature to which the product is heated in the heating station.

53. A method as claimed in claim 40, wherein the manufacturing line includes a station at which a plurality of metal powders are blended together with a binder and subsequently deposited on a conveyor belt, the method including using the controller to regulate process variables including degree of blending of the blended powders, homogeneity of the blended powders, composition of the blended powders, thickness of the blended powder deposited on the conveyor belt, amount of the blended powder deposited on the conveyor belt, and/or speed of the conveyor belt.

54. A method as claimed in claim 40, wherein the product is heated to a temperature no greater than 100° C. and the detector comprises a camera having a pixel array which generates decay curve data corresponding to a decay curve for each pixel of the pixel array, the method including using the computer to analyze the decay curve data and determine if the determined physical characteristic is outside the range of predetermined values.

55. A method as claimed in claim 40, wherein the thermal gradient is produced by an endothermic or exothermic chemical reaction in the product.

56. An apparatus for improving product quality by detecting the location of flaws in a product produced during manufacture thereof, comprising:

a central process controller including hardware and/or software effective to control one or more process variables during manufacture of a product in a manufacturing line;

a thermal gradient initiator which provides a thermal gradient within the product at a location along the manufacturing line;

a plurality of infrared detectors positioned to receive a thermographic image of the product at or downstream of the thermal gradient initiator, the infrared detectors including an infrared detector positioned to receive transmitted pulsed radiation, and an infrared detector positioned to receive transmitted unpulsed radiation;

a computer including hardware and/or software to communicate with the central process controller, receive and analyze the image from the infrared detector, and determine locations of flaws in the product on the basis of at least one determined physical characteristic of the product, and output data corresponding to the determined physical characteristic to the central process controller, the central process controller recording the location of flaws when the determined physical characteristic is outside a range of predetermined values for the physical characteristic.

57. An apparatus for improving product quality by detecting the location of flaws in a product produced during manufacture thereof, comprising:

a central process controller including hardware and/or software effective to control one or more process variables during manufacture of a product in a manufacturing line;

a thermal gradient initiator which provides a thermal gradient within the product at a location along the manufacturing line;

at least one infrared detector positioned to receive a thermographic image of the product at or downstream of the thermal gradient initiator, the detector outputting early time data and later time data corresponding to a time decaying image of the product;

a computer including hardware and/or software to communicate with the central process controller, receive and analyze the image from the infrared detector, and determine locations of flaws in the product on the basis of at least one determined physical characteristic of the product, and output data corresponding to the determined physical characteristic to the central process controller, the central process controller recording the location of flaws when the determined physical characteristic is outside a range of predetermined values for the physical characteristic, the computer determining a first physical characteristic of the product on the basis of the early time data, and the computer determining a second physical characteristic on the basis of the first physical characteristic and the later time data.

58. An apparatus as claimed in claim 57, wherein the first physical characteristic is composition of the product and the second physical characteristic is thickness of the product.

59. An apparatus for inspecting a sheet material produced by a production process, comprising:

a source of incident radiation which impinges upon the sheet material;

a conveyor for moving the sheet material in a single plane;

at least one infrared detector located proximate to a surface of the sheet material, the infrared detector being positioned downstream from the source of incident radiation and operable to create an image of the surface of the sheet material; and a computer which is in communication with the infrared detector and configured to receive and analyze the image from the infrared detector to determine physical characteristics of the sheet material, and transmit the determined physical characteristics to a controller;

wherein the infrared detector outputs early time data and later time data corresponding to a time decaying image of the sheet material, and the computer determines a first physical characteristic of the sheet material on the basis of the early time data, and a second physical characteristic of the sheet material on the basis of the first physical characteristic and the later time data.

60. An apparatus for inspecting a sheet material produced by a production process, comprising:

a central process controller configured to control at least one aspect of the production process;

a plurality of sources of incident radiation which impinge upon the sheet material, at least one of which is pulsed;

a conveyor for moving the sheet material in a single plane at a predetermined speed;

a plurality of infrared detectors located proximate to a surface of the sheet material, the infrared detectors being positioned downstream from the sources of incident radiation and operable to create images of the surface of the sheet material; and a computer which is in communication with the central process controller and configured to receive and analyze the images from the infrared detectors to determine physical characteristics of the sheet material, and transmit the determined physical characteristics to the central process controller so that the central process controller adjusts the at least one aspect of the production process in response to the determined physical characteristic;

wherein the infrared detectors output early time data and later time data corresponding to a time decaying image of the sheet material, and the computer determines a first physical characteristic of the sheet material on the basis of the early time data, and a second physical characteristic of the sheet material on the basis of the first physical characteristic and the later time data.

61. A method of determining one or more characteristics of a sheet material produced in a continuous process, comprising:

bombarding the sheet material with incident radiation from a continuous source and a pulsed source of radiation;

translating the sheet material in a single plane at a predetermined speed;

detecting infrared emissions from the sheet material from a plurality of infrared detectors; and analyzing the received radiation to determine at least one characteristic selected from the group consisting of density and thickness;

wherein the infrared detectors output early time data and later time data corresponding to a time decaying image of the sheet material, and the analyzing comprises determining a first physical characteristic of the sheet material on the basis of the early time data, and a second physical characteristic on the basis of the first physical characteristic and the later time data.

62. A method of determining one or more characteristics of a sheet material produced in a continuous process, comprising:

bombarding the sheet material with incident radiation;

translating the sheet material in a single plane at a predetermined speed;

detecting infrared emissions from the sheet material from a plurality of infrared detectors wherein at least one detector is positioned to receive reflected radiation and one detector is positioned to receive transmitted radiation; and analyzing the received radiation to determine at least one characteristic selected from the group consisting of density and thickness;

wherein the infrared detectors output early time data and later time data corresponding to a time decaying image of the sheet material, and the analyzing comprises determining a first physical characteristic of the sheet material on the basis of the early time data, and a second physical characteristic of the sheet material on the basis of the first physical characteristic and the later time data.

63. An apparatus for improving product quality by controlling one or more process variables as a function of at least one product characteristic monitored during manufacture thereof, comprising:

a central process controller including hardware and/or software effective to control one or more process variables during manufacture of a product in a manufacturing line;

a thermal gradient initiator which provides a thermal gradient within the product at a location along the manufacturing line;

at least one infrared detector positioned to receive a thermographic image of the product at or downstream of the thermal gradient initiator, and a computer including hardware and/or software to communicate with the central process controller, receive and analyze the image from the infrared detector, and determine at least one physical characteristic of the product, and output data corresponding to the determined physical characteristic to the central process controller, the central process controller modifying one or more of the process variables when the determined physical characteristic is outside a range of predetermined values for the physical characteristic;

wherein the infrared detector outputs early time data and later time data corresponding to a time decaying image of the product, and the computer determines a first physical characteristic of the product on the basis of the early time data, and a second physical characteristic of the product on the basis of the first physical characteristic and the later time data.

64. A method for improving product quality by controlling one or more process variables as a function of at least one product characteristic monitored during manufacture thereof, comprising:

controlling process variables in a process of manufacturing a product in a manufacturing line by a central process controller;

heating or cooling the product so as to provide a thermal gradient within the product at a first location along the manufacturing line;

using an infrared detector to detect infrared radiation emitted from the product at or downstream of the first location and generating a thermographic image from the detected infrared radiation;

using a computer to communicate with the central process controller, receive and analyze the image from the infrared detector, and determine at least one physical characteristic of the product; and using the computer to output data corresponding to the determined physical characteristic to the central process controller such that the central process control modifies one or more of the process variables when the determined physical characteristic is outside a range of predetermined values for the physical characteristic;

wherein the infrared detector outputs early time data and later time data corresponding to a time decaying image of the product, and the computer determines a first physical characteristic of the product on the basis of the early time data, and a second physical characteristic of the product on the basis of the first physical characteristic and the later time data.

\* \* \* \* \*